(12) United States Patent
Kitamura et al.

(10) Patent No.: US 9,447,111 B2
(45) Date of Patent: Sep. 20, 2016

(54) ORGANIC THIN FILM TRANSISTOR, ORGANIC SEMICONDUCTOR THIN FILM, AND ORGANIC SEMICONDUCTOR MATERIAL

(71) Applicant: FUJIFILM Corporation, Tokyo (JP)

(72) Inventors: Tetsu Kitamura, Ashigarakami-gun (JP); Koji Takaku, Ashigarakami-gun (JP); Wataru Sotoyama, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/685,894

(22) Filed: Apr. 14, 2015

(65) Prior Publication Data

US 2015/0218184 A1      Aug. 6, 2015

Related U.S. Application Data

(63) Continuation of application No. PCT/JP2013/077020, filed on Oct. 4, 2013.

(30) Foreign Application Priority Data

Oct. 15, 2012   (JP) ................................. 2012-227654

(51) Int. Cl.
*H01L 51/00* (2006.01)
*C07D 493/04* (2006.01)
(Continued)

(52) U.S. Cl.
CPC ........... *C07D 493/04* (2013.01); *C07F 7/0852* (2013.01); *C09D 125/06* (2013.01);
(Continued)

(58) Field of Classification Search
CPC .................................................. H01L 51/0073
See application file for complete search history.

(56) References Cited

U.S. PATENT DOCUMENTS

| 8,946,688 B2 * | 2/2015 | Sunagawa | ............ | C07D 487/04 |
| | | | | 257/40 |
| 2008/0193797 A1* | 8/2008 | Heil | ........................ | C07C 13/62 |
| | | | | 428/690 |

(Continued)

FOREIGN PATENT DOCUMENTS

| JP | 2009-267134 A | 11/2009 | |
| JP | 2010-059147 A | 3/2010 | |
| JP | 2012-513459 A | 6/2012 | |
| WO | WO 2011074232 A1 * | 6/2011 | ........... C07D 487/04 |

OTHER PUBLICATIONS

International Search Report; PCT/JP2013/077020; Dec. 24, 2013.
Written Opinion of the International Searching Authority; PCT/JP2013/077020; Dec. 24, 2013.
(Continued)

*Primary Examiner* — Brieann R Fink
(74) *Attorney, Agent, or Firm* — Studebaker & Brackett PC

(57) ABSTRACT

An organic thin film transistor containing a compound represented by the formula (1) in a semiconductor active layer has a high carrier mobility and a small fluctuation of the threshold voltage after repeated driving. $R^1$ to $R^{12}$ represent a hydrogen atom or a substituent, provided that at least one of $R^1$ to $R^{12}$ represents a substituent represented by the formula (W), or all of $R^1$ to $R^{12}$ represent a hydrogen atom. * represents a position bonded to the naphthobisbenzofuran skeleton. L represents a single bond, a divalent linking group, an oligoethyleneoxy group having a repeating number of an ethyleneoxy unit of 2 or more, or an oligosiloxane group having 2 or more silicon atoms.

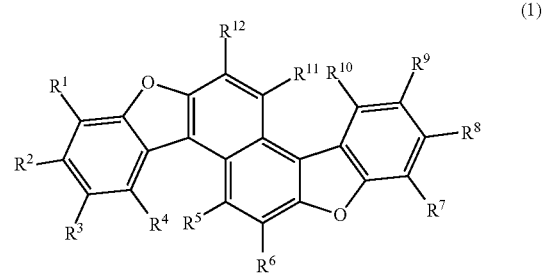

14 Claims, 1 Drawing Sheet

(51) Int. Cl.
- C07F 7/08 (2006.01)
- C09D 125/06 (2006.01)
- H01L 51/05 (2006.01)

(52) U.S. Cl.
CPC ....... H01L51/0035 (2013.01); H01L 51/0068 (2013.01); H01L 51/0073 (2013.01); H01L 51/0074 (2013.01); H01L 51/0094 (2013.01); H01L 51/006 (2013.01); H01L 51/0059 (2013.01); H01L 51/0061 (2013.01); H01L 51/0558 (2013.01)

(56) References Cited

U.S. PATENT DOCUMENTS

2010/0032658 A1* 2/2010 Lee .................. C09K 11/06 257/40

2011/0253944 A1 10/2011 Han et al.

OTHER PUBLICATIONS

K. Takimiya et al.; "Thienoacene-Based Organic Semiconductors"; Advance Materials 2011; vol. 23; pp. 4347-4370.

* cited by examiner

ORGANIC THIN FILM TRANSISTOR, ORGANIC SEMICONDUCTOR THIN FILM, AND ORGANIC SEMICONDUCTOR MATERIAL

CROSS-REFERENCE TO RELATED APPLICATIONS

This application is a Continuation of PCT International Application No. PCT/JP2013/077020, filed on Oct. 4, 2013, which claims priority under 35 U.S.C. Section 119 (a) to Japanese Patent Application No. 2012-227654 filed on Oct. 15, 2012. Each of the above applications is hereby expressly incorporated by reference, in its entirety, into the present application.

BACKGROUND OF THE INVENTION

1. Field of the Invention

The present invention relates to an organic thin film transistor, an organic semiconductor thin film, and an organic semiconductor material. More specifically, the invention relates to a compound having a naphthobisbenzofuran (which may be hereinafter referred to as NBBF) structure, an organic thin film transistor containing the compound, an organic semiconductor material for a non-light emitting organic semiconductor device containing the compound, a material for an organic thin film transistor containing the compound, a coating solution for a non-light emitting organic semiconductor device containing the compound, and an organic semiconductor thin film for a non-light emitting organic semiconductor device containing the compound.

2. Background Art

A device using an organic semiconductor material is expected to have various advantages as compared to an ordinary device using an inorganic semiconductor material, such as silicon, and thus is receiving much attention. Examples of the device using an organic semiconductor material include a photoelectric conversion device, such as an organic thin film solar cell and a solid state image sensing device, using an organic semiconductor material as a photoelectric conversion material, and a non-light emitting organic transistor. The device using an organic semiconductor material has a possibility that a device having a large area may be produced at a low temperature and a low cost, as compared to a device using an inorganic semiconductor material. Furthermore, the characteristics of the material may be easily changed by changing the molecular structure thereof, and thus there is a wide range of variations in materials, by which functions and devices that have not been achieved by an inorganic semiconductor material may be realized.

For example, Patent Reference 1 describes a compound having a naphthobisbenzofuran structure and having a diarylamino group and an aryl group as a substituent thereof, and also describes that the compound used as a light emitting material for organic electroluminescence (which may be referred to as organic EL) is excellent in the light emission efficiency of blue light and is also excellent in the operation lifetime of the organic EL device. However, Patent Reference 1 does not describe or suggest an application thereof to an organic transistor.

Patent Reference 2 describes an organic transistor containing a compound having a naphthobisbenzothiophene structure instead of a naphthobisbenzofuran structure, and describes that an organic transistor that has a high mobility and a large current on/off ratio and is excellent in storage stability may be provided.

Patent Reference 3 describes naphthobisbenzopyrrole as an organic semiconductor compound instead of a naphthobisbenzofuran structure, and describes that the compound has a large solubility to an organic solvent. Patent Reference 3 describes that the organic semiconductor compound may be applied to various purposes, and describes that the compound may be applied to a thin film transistor (TFT). However, the examples thereof only describe an example of production of a solar cell, but do not describe an example of production of an organic thin film transistor.

CITATION LIST

Patent References

Patent Reference 1: JP-A-2010-59147
Patent Reference 2: JP-A-2009-267134
Patent Reference 3: JP-A-2012-513459

SUMMARY OF INVENTION

It has been known that a polycyclic condensed compound containing an aromatic heterocyclic ring is useful as a material for an organic EL device, as described in Patent Reference 1. However, it may not be said that a compound that is useful as a material for an organic EL device is immediately useful as a semiconductor material for an organic thin film transistor. This is because there is a difference in the characteristics demanded for the organic compound between an organic EL device and an organic thin film transistor. An organic EL device generally requires charge transport in the thickness direction of the thin film (which is generally from several nanometers to several hundred nanometers), whereas an organic thin film transistor requires charge (carrier) transport in a long distance between electrodes in the plane direction of the thin film, which is generally from several micrometers to several hundred micrometers. Accordingly, the demanded carrier mobility is considerably high. Thus, as a semiconductor material for an organic thin film transistor, an organic compound that has a high alignment order of molecules with high crystallinity is demanded. Furthermore, for achieving a high carrier mobility, the π-conjugate plane is preferably perpendicular to the substrate. In an organic EL device, on the other hand, a device that has a high light emission efficiency and uniform in-plane light emission is demanded for enhancing the light emission efficiency. In general, an organic compound having high crystallinity may be a cause of light emission defects, such as in-plane electric field unevenness, in-plane light emission unevenness and light emission quenching, and thus the material for an organic EL device is demanded to have high amorphous property with low crystallinity. Accordingly, even when an organic compound constituting a material for an organic EL device is diverted to an organic semiconductor material, good transistor characteristics may not immediately obtained.

Actually, the present inventors apply the polycyclic condensed compound containing an aromatic heterocyclic ring applied to an organic EL device and a solar cell described in Patent References 1 and 3 to an organic thin film transistor, but it has been found that there is a problem that sufficient transistor characteristics are not obtained. Specifically, in the case where the compound that is described with a specific structure thereof in Patent References is applied as an organic semiconductor material to an organic thin film transistor, the investigations made by the inventors reveal that a high carrier mobility is not obtained.

When the compound used in an organic thin film transistor in Patent Reference 2 is applied as an organic semiconductor material to an organic thin film transistor, the investigations made by the inventors reveal that the carrier mobility is insufficient, and the fluctuation of the threshold voltage becomes large in repeated driving. The large fluctuation of the threshold voltage brings about a problem that the transistor is deteriorated in reliability and may not be used for a prolonged period of time. The fluctuation of the threshold voltage after repeated driving is a problem that has not been known in the art.

Under the circumstances, the inventors have made investigations for solving the problems in the related art. An object to be achieved by the invention is to provide an organic thin film transistor that has a high carrier mobility and a small fluctuation of the threshold voltage after repeated driving.

As a result of earnest investigations for solving the problems, the inventors have found that unsubstituted NBBF or an NBBF derivative having a substituent having a particular structure has high crystallinity and forms an organic thin film that is advantageous for carrier transport. It has been found that an organic thin film transistor having a high carrier mobility is obtained thereby.

Furthermore, the inventors have found that an organic thin film transistor that uses unsubstituted NBBF, NBBF having a substituent having a particular structure, or a derivative thereof in a semiconductor active layer shows a small fluctuation of the threshold voltage after repeated driving, and thus have completed the invention.

The invention as a specific measure for solving the problems includes the following aspects. (1) An organic thin film transistor containing a compound represented by the following formula (1) in a semiconductor active layer:

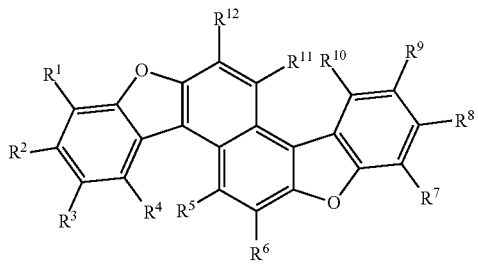

Formula (1)

wherein $R^1$ to $R^{12}$ each independently represent a hydrogen atom or a substituent, provided that at least one of $R^1$ to $R^{12}$ represents a substituent represented by the following formula (W), or all of $R^1$ to $R^{12}$ represent a hydrogen atom:

*-L-R     Formula (W)

wherein * represents a position bonded to the naphthobisbenzofuran skeleton; L represents a single bond, a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group having 2 or more carbon atoms, an oligoethyleneoxy group having a repeating number of an ethyleneoxy unit of 2 or more, or an oligosiloxane group having 2 or more silicon atoms:

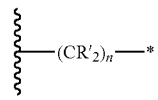 (L-1)

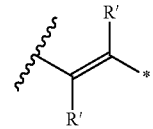 (L-2)

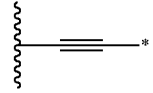 (L-3)

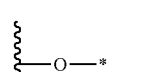 (L-4)

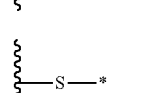 (L-5)

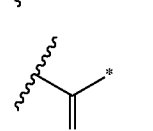 (L-6)

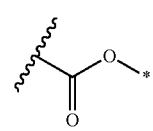 (L-7)

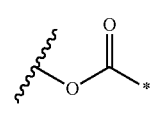 (L-8)

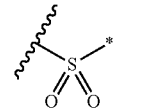 (L-9)

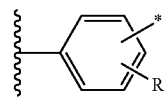 (L-10)

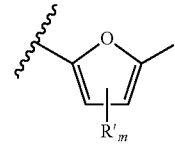 (L-11)

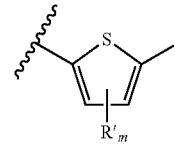 (L-12)

wherein in the formulae (L-1) to (L-12), the wavy line represents a position bonded to the naphthobisbenzofuran skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-2), (L-10), (L-11) and (L-12), R' each independently represent a hydrogen atom or a substituent.

(2) In the organic thin film transistor according to the item (1), at least one of $R^2$, $R^3$, $R^8$ and $R^9$ preferably represents a substituent represented by the formula (W).

(3) In the organic thin film transistor according to the item (1), the compound represented by the formula (1) is preferably a compound represented by the following formula (2-1) or (2-2):

Formula (2-1)

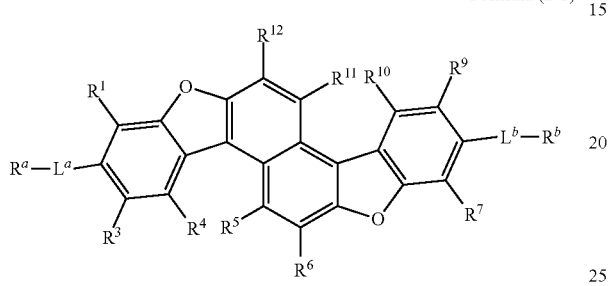

wherein $R^1$, $R^3$ to $R^7$, and $R^9$ to $R^{12}$ each independently represent a hydrogen atom or a substituent; $L^a$ and $L^b$ each independently represent a single bond, a divalent linking group represented by any one of the following formulae (L-1) to (L-12), or a divalent linking group containing 2 or more divalent linking groups each represented by any one of the following formulae (L-1) to (L-12) bonded to each other; and $R^a$ and $R^b$ each independently represent a substituted or unsubstituted alkyl group having 2 or more carbon atoms, an oligoethyleneoxy group having a repeating number of an ethyleneoxy unit of 2 or more, or an oligosiloxane group having 2 or more silicon atoms, Formula (2-2)

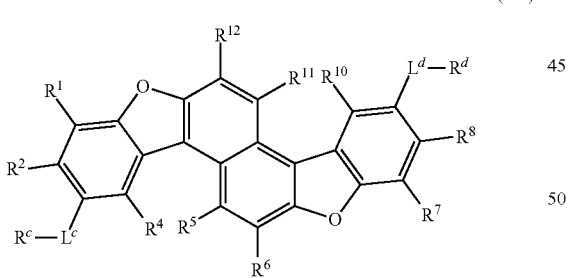

wherein $R^1$, $R^2$, $R^4$ to $R^8$, and $R^{10}$ to $R^{12}$ each independently represent a hydrogen atom or a substituent; $L^c$ and $L^d$ each independently represent a single bond, a divalent linking group represented by any one of the following formulae (L-1) to (L-12), or a divalent linking group containing 2 or more divalent linking groups each represented by any one of the following formulae (L-1) to (L-12) bonded to each other; and $R^c$ and $R^d$ each independently represent a substituted or unsubstituted alkyl group having 2 or more carbon atoms, an oligoethyleneoxy group having a repeating number of an ethyleneoxy unit of 2 or more, or an oligosiloxane group having 2 or more silicon atoms,

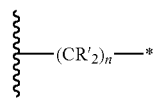 (L-1)

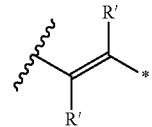 (L-2)

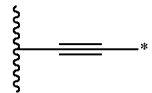 (L-3)

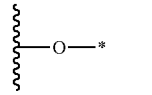 (L-4)

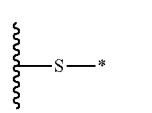 (L-5)

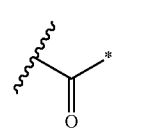 (L-6)

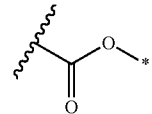 (L-7)

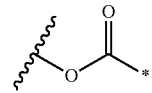 (L-8)

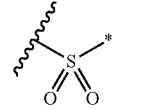 (L-9)

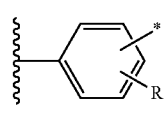 (L-10)

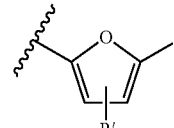 (L-11)

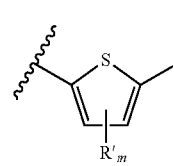 (L-12)

wherein in the formulae (L-1) to (L-12), the wavy line represents a position bonded to the naphthobisbenzofuran skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-2), (L-10), (L-11) and (L-12), R' each independently represent a hydrogen atom or a substituent.

(4) In the organic thin film transistor according to the item (3), in the formula (2-1) or (2-2), $R^a$, $R^b$, $R^c$ and $R^d$ preferably represent an alkyl group having 2 or more carbon atoms.

(5) In the organic thin film transistor according to the item (3), in the formula (2-1) or (2-2), $R^a$, $R^b$, $R^c$ and $R^d$ preferably represent a linear alkyl group having from 6 to 12 carbon atoms.

(6) In the organic thin film transistor according to any one of the items (3) to (5), in formula (2-1) or (2-2), $L^a$, $L^b$, $L^c$ and $L^d$ preferably represent a single bond.

(7) A compound represented by the following formula (I):

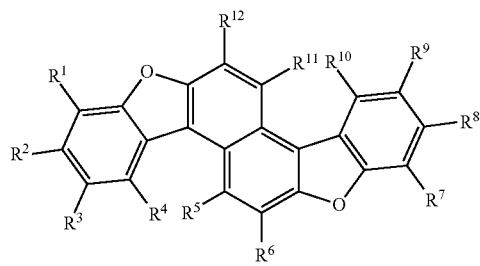

Formula (1)

wherein $R^1$ to $R^{12}$ each independently represent a hydrogen atom or a substituent, provided that at least one of $R^1$ to $R^{12}$ represents a substituent represented by the following formula (W), or all of $R^1$ to $R^{12}$ represent a hydrogen atom:

*-L-R    Formula (W)

wherein * represents a position bonded to the naphthobisbenzofuran skeleton; L represents a single bond, a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group having 2 or more carbon atoms, an oligoethyleneoxy group having a repeating number of an ethyleneoxy unit of 2 or more, or an oligosiloxane group having 2 or more silicon atoms:

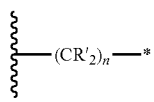

(L-1)

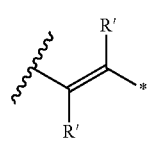

(L-2)

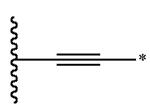

(L-3)

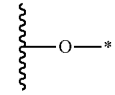

(L-4)

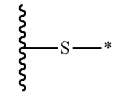

(L-5)

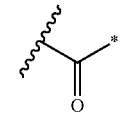

(L-6)

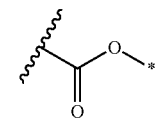

(L-7)

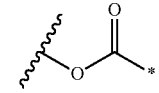

(L-8)

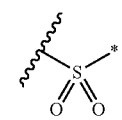

(L-9)

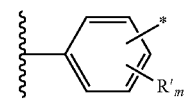

(L-10)

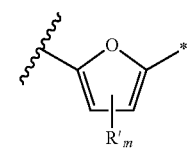

(L-11)

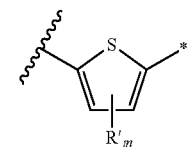

(L-12)

wherein in the formulae (L-1) to (L-12), the wavy line represents a position bonded to the naphthobisbenzofuran skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-2), (L-10), (L-11) and (L-12), R' each independently represent a hydrogen atom or a substituent.

(8) In the compound according to the item (7), at least one of $R^2$, $R^3$, $R^8$ and $R^9$ preferably represents a substituent represented by the formula (W).

(9) In the compound according to the item (7), the compound represented by the formula (1) is preferably a compound represented by the following formula (2-1) or (2-2):

Formula (2-1)

[Chemical structure of naphthobisbenzofuran with substituents $R^1$, $R^3$ to $R^7$, $R^9$ to $R^{12}$, and groups $R^a-L^a$ and $L^b-R^b$]

wherein $R^1$, $R^3$ to $R^7$, and $R^9$ to $R^{12}$ each independently represent a hydrogen atom or a substituent; $L^a$ and $L^b$ each independently represent a single bond, a divalent linking group represented by any one of the following formulae (L-1) to (L-12), or a divalent linking group containing 2 or more divalent linking groups each represented by any one of the following formulae (L-1) to (L-12) bonded to each other; and $R^a$ and $R^b$ each independently represent a substituted or unsubstituted alkyl group having 2 or more carbon atoms, an oligoethyleneoxy group having a repeating number of an ethyleneoxy unit of 2 or more, or an oligosiloxane group having 2 or more silicon atoms, Formula (2-2)

[Chemical structure of naphthobisbenzofuran with substituents $R^1$, $R^2$, $R^4$ to $R^8$, $R^{10}$ to $R^{12}$, and groups $R^c-L^c$ and $L^d-R^d$]

wherein $R^1$, $R^2$, $R^4$ to $R^8$, and $R^{10}$ to $R^{12}$ each independently represent a hydrogen atom or a substituent; $L^c$ and $L^d$ each independently represent a single bond, a divalent linking group represented by any one of the following formulae (L-1) to (L-12), or a divalent linking group containing 2 or more divalent linking groups each represented by any one of the following formulae (L-1) to (L-12) bonded to each other; and $R^c$ and $R^d$ each independently represent a substituted or unsubstituted alkyl group having 2 or more carbon atoms, an oligoethyleneoxy group having a repeating number of an ethyleneoxy unit of 2 or more, or an oligosiloxane group having 2 or more silicon atoms, (L-1)

$-(CR'_2)_n-*$ (L-2)

[structure: C=C with R' substituents]

(L-3)

[structure: C≡C]

(L-4)

$-O-*$ (L-5)

$-S-*$ (L-6)

[structure: C(=O)-]

(L-7)

[structure: C(=O)-O-]

(L-8)

[structure: O-C(=O)-O-]

(L-9)

[structure: -S(=O)₂-]

(L-10)

[phenylene structure with $R'_m$]

(L-11)

[furan-2,5-diyl structure with $R'_m$]

(L-12)

[thiophene-2,5-diyl structure with $R'_m$]

wherein in the formulae (L-1) to (L-12), the wavy line represents a position bonded to the naphthobisbenzofuran skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-2), (L-10), (L-11) and (L-12), R' each independently represent a hydrogen atom or a substituent.

(10) In the compound according to the item (9), in the formula (2-1) or (2-2), $R^a$, $R^b$, $R^c$ and $R^d$ preferably represent an alkyl group having 2 or more carbon atoms.

(11) In the compound according to the item (9), in the formula (2-1) or (2-2), $R^a$, $R^b$, $R^c$ and $R^d$ preferably represent a linear alkyl group having from 6 to 12 carbon atoms.

(12) In the compound according to any one of the items (9) to (12), in formula (2-1) or (2-2), $L^a$, $L^b$, $L^c$ and $L^d$ preferably represent a single bond.

(13) An organic semiconductor material for a non-light emitting organic semiconductor device, containing the compound represented by the formula (1) according to any one of the items (7) to (12).

(14) A material for an organic thin film transistor, containing the compound represented by the formula (1) according to any one of the items (7) to (12).

(15) A coating solution for a non-light emitting organic semiconductor device, containing the compound represented by the formula (1) according to any one of the items (7) to (12).

(16) A coating solution for a non-light emitting organic semiconductor device, containing the compound represented by the formula (1) according to any one of the items (7) to (12), and a polymer binder.

(17) An organic semiconductor thin film for a non-light emitting organic semiconductor device, containing the compound represented by the formula (1) according to any one of the items (7) to (12).

(18) An organic semiconductor thin film for a non-light emitting organic semiconductor device, containing the compound represented by the formula (1) according to any one of the items (7) to (12), and a polymer binder.

(19) The organic semiconductor thin film for a non-light emitting organic semiconductor device according to the item (17) or (18) is preferably produced by a solution coating method.

According to the invention, an organic thin film transistor may be provided that has a high carrier mobility and a small fluctuation of the threshold voltage after repeated driving.

DESCRIPTION OF EMBODIMENTS

Figure 1:
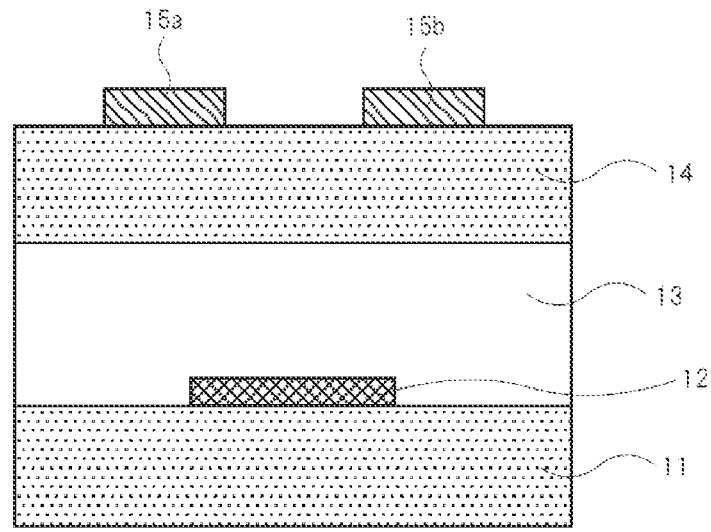
FIG. 1 is a schematic illustration showing a cross sectional structure of one example of the organic thin film transistor of the invention.

The invention will be described in detail below. The description for the constitutional components shown below may be made with reference to representative embodiments and specific examples, but the invention is not limited to the embodiments and the examples. In the description, a numerical range expressed with reference to an upper limit and/or a lower limit means a range that includes the upper limit and/or the lower limit.

In the invention, the hydrogen atom that is referred without any particular discrimination in the description of the formulae herein includes isotopes thereof (such as a deuterium atom). The atoms constituting the substituents also include isotopes thereof.

Organic Thin Film Transistor

The organic thin film transistor of the invention contains a compound represented by the following formula (1) in a semiconductor active layer:

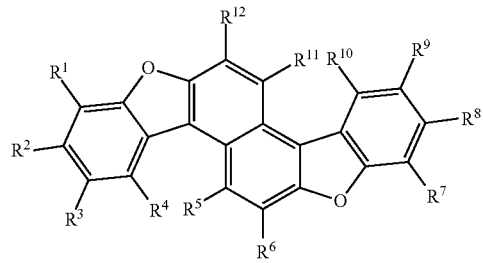

Formula (1)

wherein in the formula (1), $R^1$ to $R^{12}$ each independently represent a hydrogen atom or a substituent, provided that at least one of $R^1$ to $R^{12}$ represents a substituent represented by the following formula (W), or all of $R^1$ to $R^{12}$ represent a hydrogen atom:

*-L-R    Formula (W)

wherein in the formula (W), * represents a position bonded to the naphthobisbenzofuran skeleton; L represents a single bond, a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group having 2 or more carbon atoms, an oligoethyleneoxy group having a repeating number of an ethyleneoxy unit of 2 or more, or an oligosiloxane group having 2 or more silicon atoms:

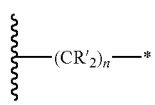

(L-1)

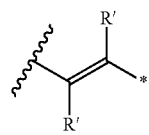

(L-2)

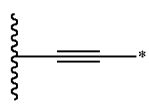

(L-3)

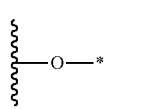

(L-4)

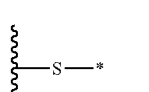

(L-5)

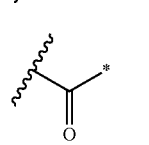

(L-6)

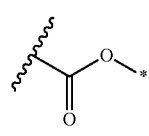

(L-7)

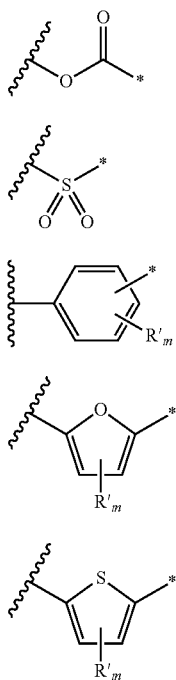

wherein in the formulae (L-1) to (L-12), the wavy line represents a position bonded to the naphthobisbenzofuran skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-2), (L-10), (L-11) and (L-12), R' each independently represent a hydrogen atom or a substituent.

According to the constitution, the organic thin film transistor of the invention has a high carrier mobility and a small fluctuation of the threshold voltage after repeated driving.

The compound represented by the formula (1) has high crystallinity and is capable of providing a semiconductor material forming an organic thin film that is advantageous for carrier transport. Accordingly, an organic thin film transistor having a high carrier mobility may be obtained.

For reducing the fluctuation of the threshold voltage after repeated driving, there are such requirements as chemical stability of the organic semiconductor material (particularly, air oxidation resistance and redox stability), thermal stability in the form of a thin film, a large film density capable of preventing air and water from invading, a film quality with less defects capable of preventing charges from being accumulated, and the like. It is considered that the compound represented by the formula (1) satisfies these requirements and thus has a small fluctuation of the threshold voltage after repeated driving. Accordingly, the organic thin film transistor of the invention having a less fluctuation of the threshold voltage after repeated driving has a semiconductor active layer that has the chemical stability, the film density, and the like, and thus effectively functions as a transistor for a prolonged period of time.

Most of the known compounds having a structure that is analogous to naphthobisbenzofuran (NBBF) contain a chalcogen element (such as S and Se), and for example, Patent Reference 2 describes naphthobisbenzothiophene. However, a compound containing a chalcogen element (such as S and Se) is difficult to provide an organic thin film that has good film quality and molecular packing advantageous for carrier transport.

The invention uses, as an organic semiconductor material, a compound that has the naphthobisbenzofuran (NBBF) structure or the derivative structure thereof containing oxygen atoms and has the substituent having the particular structure, as represented by the formula (1). It is considered that the organic semiconductor material using the compound represented by the formula (1) forms a herringbone structure suitable for carrier transport and facilitates the formation of a two-dimensional orbital overlap in the organic thin film (the advantage of a herringbone structure for carrier transport is described, for example, in Adv. Mater., 2011, 23, 4347-4370). It is considered that according to the constitution, the compound of the invention achieves good film quality and a high carrier mobility and is capable of being used favorably as an organic thin film transistor.

Preferred embodiments of the compound of the invention and the organic thin film transistor of the invention will be described below.

Compound Represented by Formula (1)

The compound of the invention is represented by the following formula (1). The compound of the invention is contained in a semiconductor active layer described later in the organic thin film transistor of the invention. Thus, the compound of the invention may be used as a material for an organic thin film transistor.

Formula (1)

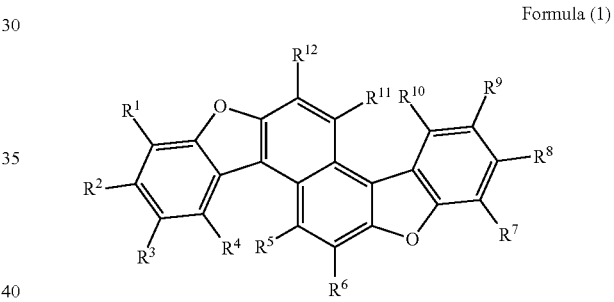

wherein in the formula (1), $R^1$ to $R^{12}$ each independently represent a hydrogen atom or a substituent, provided that at least one of $R^1$ to $R^{12}$ represents a substituent represented by the following formula (W), or all of $R^1$ to $R^{12}$ represent a hydrogen atom.

*-L-R  Formula (W)

wherein in the formula (W), * represents a position bonded to the naphthobisbenzofuran skeleton; L represents a single bond, a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group having 2 or more carbon atoms, an oligoethyleneoxy group having a repeating number of an ethyleneoxy unit of 2 or more, or an oligosiloxane group having 2 or more silicon atoms.

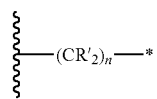

(L-1)

-continued

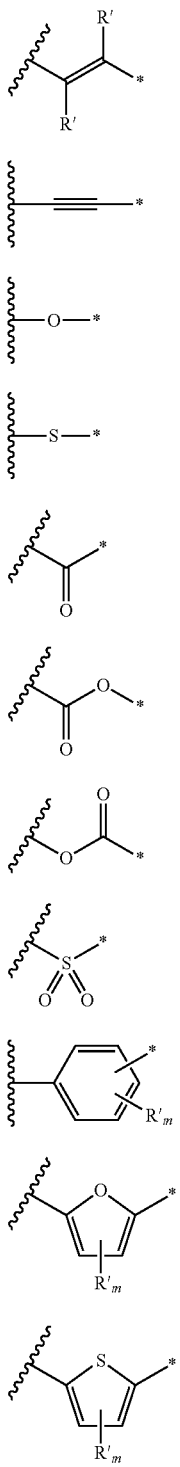

wherein in the formulae (L-1) to (L-12), the wavy line represents a position bonded to the naphthobisbenzofuran skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-2), (L-10), (L-11) and (L-12), R' each independently represent a hydrogen atom or a substituent.

In the formula (1), $R^1$ to $R^{12}$ each independently represent a hydrogen atom or a substituent. At least one of $R^1$ to $R^{12}$ represents a substituent represented by the formula (W), or all $R^1$ to $R^{12}$ each represent a hydrogen atom.

In the compound represented by the formula (1), at least one of $R^1$ to $R^{12}$ preferably represents a substituent represented by the formula (W) from the standpoint of the solution process suitability of the material and the molecular arrangement in the film. According to the constitution, the production efficiency of the organic thin film capable of being applied to an organic thin film transistor may be enhanced to suppress the production cost. Furthermore, the carrier transport characteristics, such as the carrier mobility, and the chemical and physical stability of the thin film may be also enhanced.

In the compound represented by the formula (1), all $R^1$ to $R^{12}$ each preferably represent a hydrogen atom from the standpoint of the carrier mobility rather than the solubility.

The compound represented by the formula (1) may contain a substituent other than the substituent represented by the formula (W).

Examples of the substituent that may be $R^1$ to $R^{12}$ in the formula (1) include a halogen atom, an alkyl group (including a cycloalkyl group, a bicycloalkyl group and a tricycloalkyl group), an alkenyl group (including a cycloalkenyl group and a bicycloalkenyl group), an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkyl- or arylsulfonylamino group, a mercapto group, an alkylthio group, an arylthio group, a heterocyclic thio group, a sulfamoyl group, a sulfo group, an alkyl- or arylsulfinyl group, an alkyl- or arylsulfonyl group, an acyl group, an aryloxycarbonyl group, an alkoxycarbonyl group, a carbamoyl group, an aryl- or heterocyclic azo group, an imide group, a phosphino group, a phosphinyl group, a phosphinyloxy group, a phosphinylamino group, a phosphono group, a silyl group, a hydrazino group, a ureido group, a boronic acid group (—B(OH)$_2$), a phosphato group (—PO(OH)$_2$), a sulphato group (—OSO$_3$H), and other known groups.

Among these, a halogen atom, an alkyl group and an aryl group are preferred, and a fluorine atom, an alkyl group having from 1 to 3 carbon atoms and a phenyl group are more preferred.

In the compound represented by the formula (1), the number of the substituent other than the substituent represented by the formula (W) in $R^1$ to $R^{12}$ is preferably from 0 to 4, more preferably from 0 to 2, and particularly preferably 0.

The substituent represented by the formula (W) will be described.

In the formula (W), * represents a position bonded to the naphthobisbenzofuran skeleton.

In the formula (W), L represents a single bond, a divalent linking group represented by any one of the following formulae (L-1) to (L-12), or a divalent linking group containing 2 or more divalent linking groups each represented by anyone of the following formulae (L-1) to (L-12) bonded to each other.

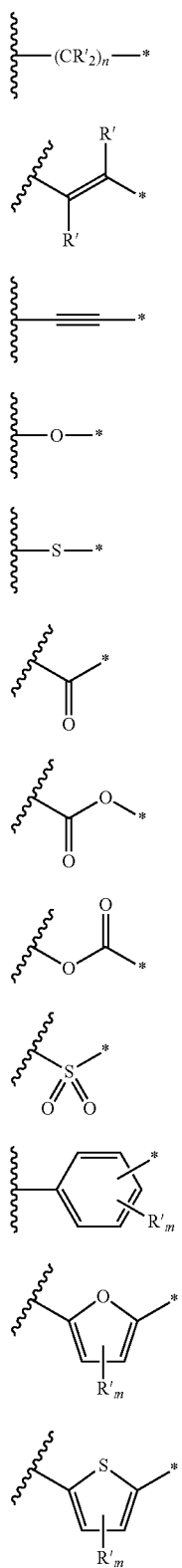

In the formulae (L-1) to (L-12), the wavy line represents a position bonded to the naphthobisbenzofuran skeleton, and * represents a position bonded to R in the formula (W). In the formula (L-1), n represents an integer of 1 or more. In the formula (L-10), m represents 4; and in the formulae (L-11) and (L-12), m represents 2. In the formulae (L-2), (L-10), (L-11) and (L-12), R' each independently represent a hydrogen atom or a substituent.

In the case where L represents a divalent linking group containing divalent linking groups each represented by any one of the formulae (L-1) to (L-12) bonded to each other, the number of the divalent linking groups each represented by any one of the formulae (L-1) to (L-12) bonded to each other is preferably from 2 to 4, and more preferably 2 or 3.

In the formulae (L-10) to (L-12), it is also preferred that any one of the formulae (L-1) to (L-12) is further inserted between * and R to form L that represents a linking group containing divalent linking groups each represented by any one of the formulae (L-1) to (L-12) bonded to each other.

In the formula (L-1), n represents an integer of 1 or more, preferably an integer of from 1 to 10, more preferably an integer of from 1 to 6, and further preferably an integer of from 1 to 3.

Examples of the substituent R' in the formulae (L-2), (L-10), (L-11) and (L-12) include the groups that are shown as examples of the other substituent that may be $R^1$ to $R^{12}$ in the formula (1).

In the formula (L-10), m represents 4; and in the formulae (L-11) and (L-12), m represents 2.

L preferably represents any one of a single bond and the formulae (L-1), (L-3), (L-4), (L-6), (L-10), (L-11) and (L-12), more preferably any one of a single bond and the formulae (L-1), (L-3), (L-4), (L-10) and (L-12), particularly preferably any one of a single bond and the formulae (L-4), (L-10) and (L-12), and most preferably a single bond from the standpoint of the chemical stability and the carrier transport property.

In the formula (W), R represents a substituted or unsubstituted alkyl group having 2 or more carbon atoms, an oligoethyleneoxy group having a repeating number of an ethyleneoxy group of 2 or more, or an oligosiloxane group having 2 or more silicon atoms.

In the case where R in the formula (W) represents a substituted or unsubstituted alkyl group having 2 or more carbon atoms, the number of carbon atoms thereof is preferably from 2 to 18, more preferably from 6 to 12 from the standpoint of the chemical stability and the carrier transport property, and further preferably from 6 to 10. The alkyl group that may be R may be any one of linear, branched and cyclic, and is preferably a linear alkyl group, more preferably a linear alkyl group having from 6 to 12 carbon atoms, and particularly preferably a linear alkyl group having from 6 to 10 carbon atoms. In the case where R represents an alkyl group having a substituent, examples of the substituent include a halogen atom, and a fluorine atom is preferred. In the case where R represents an alkyl group having a fluorine atom, the alkyl group may be a perfluoroalkyl group, in which all the hydrogen atoms of the alkyl group are replaced by fluorine atoms.

In the case where R in the formula (W) represents an oligoethyleneoxy group having a repeating number of an ethyleneoxy group of 2 or more, the oligoethyleneoxy group represented by R herein means a group represented by $(CH_2CH_2)_xOY$ (wherein the repeating number of an ethyleneoxy unit x is an integer of 2 or more, and Y as the terminal group represents a hydrogen atom or a substituent). In the case where Y as the terminal group of the oligoethyleneoxy group is a hydrogen atom, the group is a hydroxyl group. The repeating number of an ethyleneoxy unit x is preferably from 2 to 4, and more preferably from 2 to 3. The terminal hydroxyl group of the oligoethyleneoxy group is preferably blocked, i.e., Y preferably represents a substituent. In this case, the hydroxyl group is preferably blocked with an alkyl group having from 1 to 3 carbon atoms, i.e., Y preferably represents an alkyl group having from 1 to 3 carbon atoms, and Y more preferably represents a methyl group or an ethyl group.

In the case where R in the formula (W) represents an oligosiloxane group having 2 or more silicon atoms, the repeating number of a siloxane unit is preferably from 2 to 4, and more preferably from 2 to 3. The Si atom is preferably bonded to a hydrogen atom or an alkyl group. In the case where the Si atom is bonded to an alkyl group, the number of carbon atoms of the alkyl group is preferably from 1 to 3, and for example, a methyl group or an ethyl group is preferably bonded thereto. The Si atom may be bonded to the same alkyl groups or may be bonded to different alkyl groups or a hydrogen atom. The siloxane units constituting the oligosiloxane group may be all the same as each other or different from each other, and are preferably all the same as each other.

In the compound represented by the formula (1), the number of the substituent that is represented by the formula (W) in $R^1$ to $R^{12}$ is preferably from 1 to 4, more preferably from 1 to 2, and particularly preferably 2.

In the formula (1) in the invention, at least one of $R^2$, $R^3$, $R^8$ and $R^9$ preferably represents the substituent represented by the formula (W). Furthermore, two positions of any one of $R^2$ and $R^3$ and any one of $R^8$ and $R^9$ are more preferably substituted.

It is considered that the reason why these positions are preferred as the substitution positions in the formula (1) is that the compound is excellent in chemical stability and is preferred from the standpoint of the HOMO level and the molecular packing in the film. In particular, when two positions of any one of $R^2$ and $R^3$ and any one of $R^8$ and $R^9$ each represent a substituent, a high carrier concentration may be obtained.

In the invention, the compound represented by the formula (1) is preferably a compound represented by the following formula (2-1) or (2-2).

Formula (2-1)

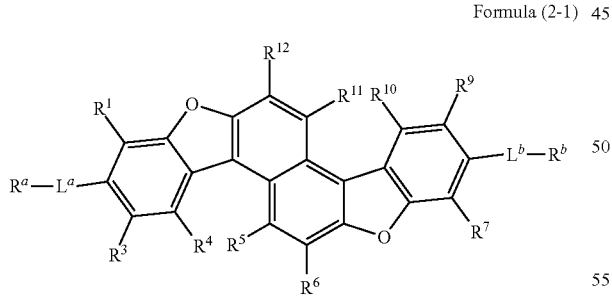

wherein in the formula (2-1), $R^1$, $R^3$ to $R^7$, and $R^9$ to $R^{12}$ each independently represent a hydrogen atom or a substituent; $L^a$ and $L^b$ each independently represent a single bond, a divalent linking group represented by any one of the following formulae (L-1) to (L-12), or a divalent linking group containing 2 or more divalent linking groups each represented by any one of the following formulae (L-1) to (L-12) bonded to each other; and $R^a$ and $R^b$ each independently represent a substituted or unsubstituted alkyl group having 2 or more carbon atoms, an oligoethyleneoxy group having a repeating number of an ethyleneoxy unit of 2 or more, or an oligosiloxane group having 2 or more silicon atoms, Formula (2-2)

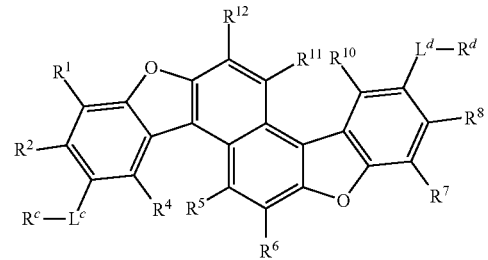

wherein in the formula (2-2), $R^1$, $R^2$, $R^4$ to $R^8$, and $R^{10}$ to $R^{12}$ each independently represent a hydrogen atom or a substituent; $L^c$ and $L^d$ each independently represent a single bond, a divalent linking group represented by any one of the following formulae (L-1) to (L-12), or a divalent linking group containing 2 or more divalent linking groups each represented by anyone of the following formulae (L-1) to (L-12) bonded to each other; and $R^c$ and $R^d$ each independently represent a substituted or unsubstituted alkyl group having 2 or more carbon atoms, an oligoethyleneoxy group having a repeating number of an ethyleneoxy unit of 2 or more, or an oligosiloxane group having 2 or more silicon atoms, (L-1)

(L-2)

(L-3)

(L-4)

(L-5)

(L-6)

(L-7)

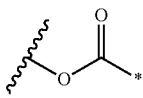
(L-8)

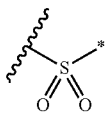
(L-9)

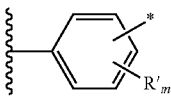
(L-10)

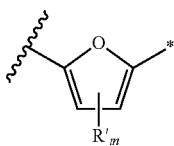
(L-11)

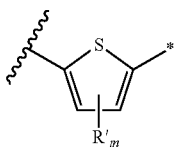
(L-12)

wherein in the formulae (L-1) to (L-12), the wavy line represents a position bonded to the naphthobisbenzofuran skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-2), (L-10), (L-11) and (L-12), R' each independently represent a hydrogen atom or a substituent.

In the formula (2-1), $R^1$, $R^3$ to $R^7$, and $R^9$ to $R^{12}$ each independently represent a hydrogen atom or a substituent. The preferred ranges of the substituents represented by $R^1$, $R^3$ to $R^7$, and $R^9$ to $R^{12}$ are the same as the preferred ranges of the substituents represented by $R^1$ to $R^{12}$ in the formula (1) other than the substituent represented by the formula (W).

In the formula (2-1), $L^a$ and $L^b$ each independently represent a single bond, a divalent linking group represented by any one of the formulae (L-1) to (L-12), or a divalent linking group containing 2 or more divalent linking groups each represented by any one of the formulae (L-1) to (L-12) bonded to each other. The preferred ranges of $L^a$ and $L^b$ are the same as the preferred ranges of L in the formula (W). $L^a$ and $L^b$ are preferably the same as each other.

In the formula (2-1), $R^a$ and $R^b$ each independently represent a substituted or unsubstituted alkyl group having 2 or more carbon atoms, an oligoethyleneoxy group having a repeating number of an ethyleneoxy unit of 2 or more, or an oligosiloxane group having 2 or more silicon atoms. The preferred ranges of $R^a$ and $R^b$ are the same as the preferred ranges of R in the formula (W). $R^a$ and $R^b$ are preferably the same as each other.

In the formula (2-2), $R^1$, $R^2$, $R^4$ to $R^8$, and $R^{10}$ to $R^{12}$ each independently represent a hydrogen atom or a substituent. The preferred ranges of the substituents represented by $R^1$, $R^2$, $R^4$ to $R^8$, and $R^{10}$ to $R^{12}$ are the same as the preferred ranges of the substituents represented by $R^1$ to $R^{12}$ in the formula (1) other than the substituent represented by the formula (W).

In the formula (2-2), $L^c$ and $L^d$ each independently represent a single bond, a divalent linking group represented by any one of the formulae (L-1) to (L-12), or a divalent linking group containing 2 or more divalent linking groups each represented by any one of the formulae (L-1) to (L-12) bonded to each other. The preferred ranges of $L^c$ and $L^d$ are the same as the preferred ranges of L in the formula (W). $L^c$ and $L^d$ are preferably the same as each other.

In the formula (2-2), $R^c$ and $R^d$ each independently represent a substituted or unsubstituted alkyl group having 2 or more carbon atoms, an oligoethyleneoxy group having a repeating number of an ethyleneoxy unit of 2 or more, or an oligosiloxane group having 2 or more silicon atoms. The preferred ranges of $R^c$ and $R^d$ are the same as the preferred ranges of R in the formula (W). $R^c$ and $R^d$ are preferably the same as each other.

In the formulae (2-1) and (2-2), all $R^a$, $R^b$, $R^c$ and $R^d$ each preferably represent an alkyl group having 2 or more carbon atoms, and more preferably a linear alkyl group having from 6 to 12 carbon atoms.

In the formulae (2-1) and (2-2), all $L^a$, $L^b$, $L^c$ and $L^d$ each preferably represent a single bond.

Specific examples of the compound represented by the formula (1) are shown below, but the compound represented by the formula (1) capable of being used in the invention is not construed as being limited to the specific examples.

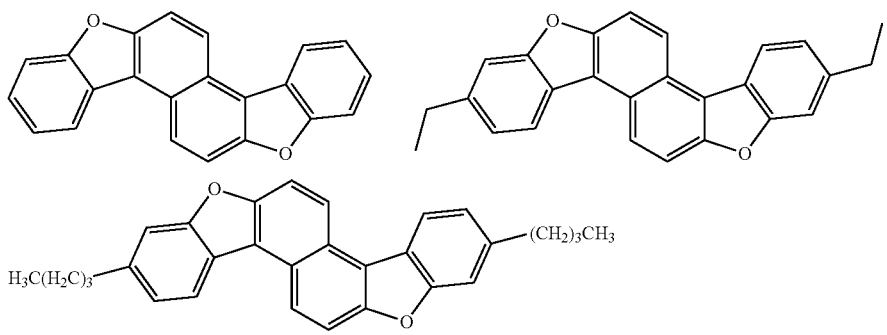

-continued
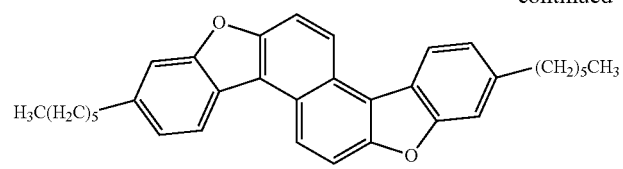
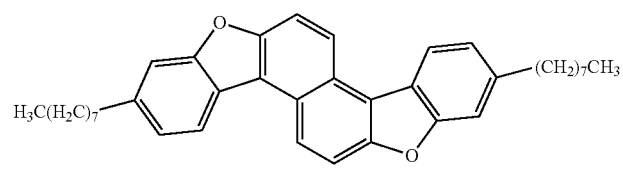
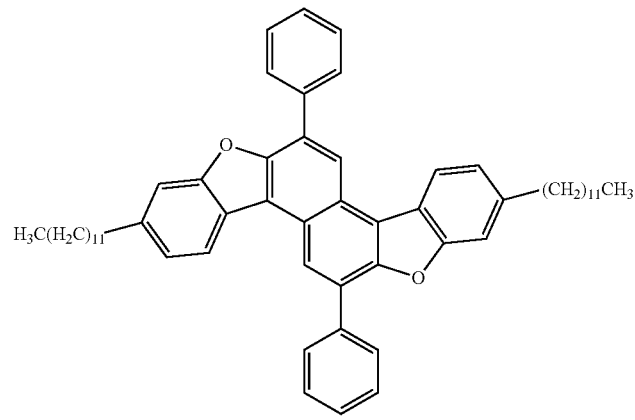
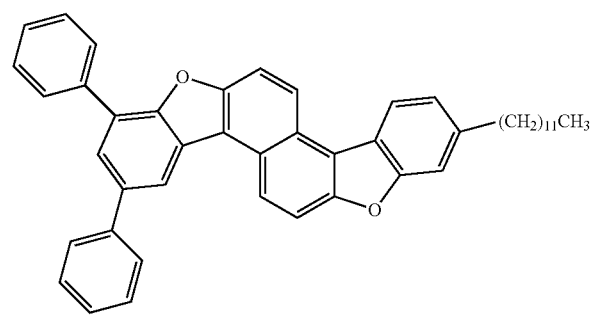
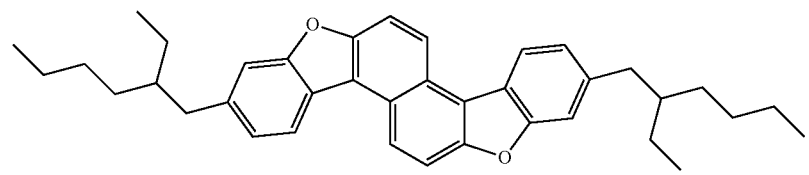
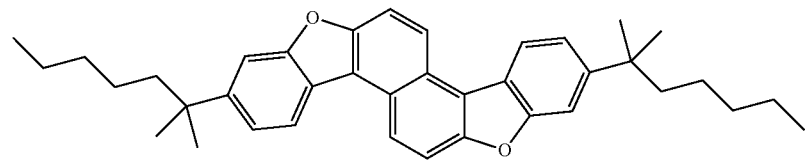
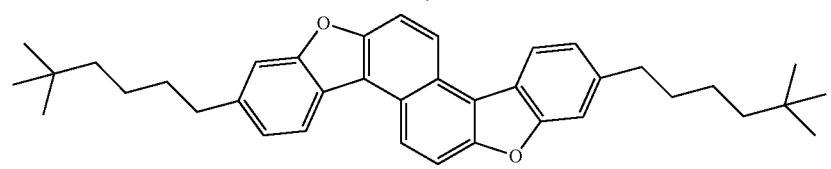
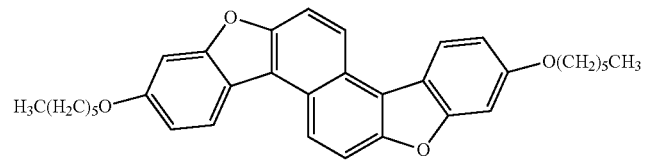

-continued
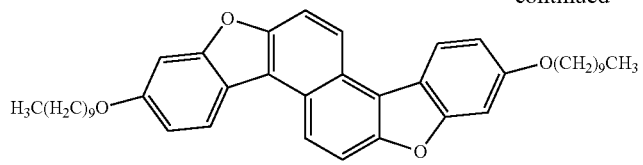
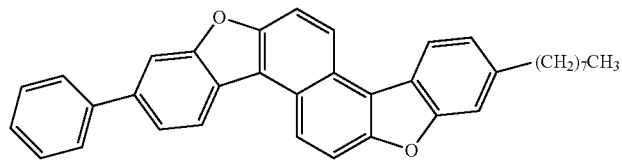
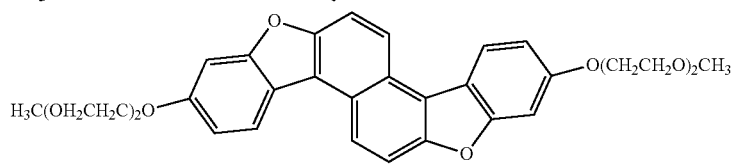
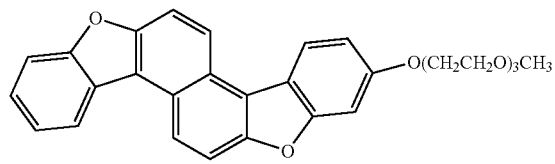
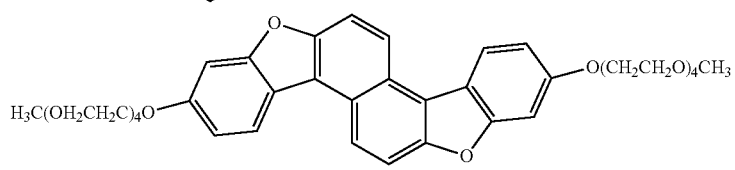
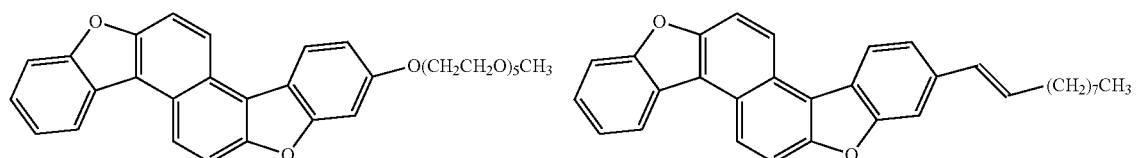
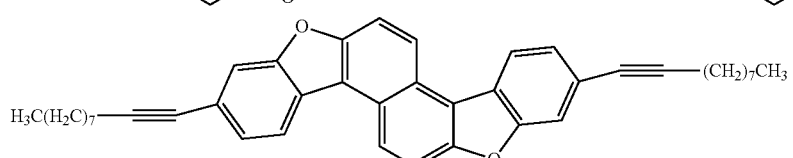
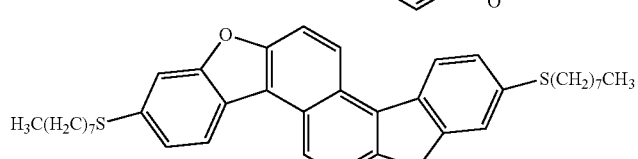
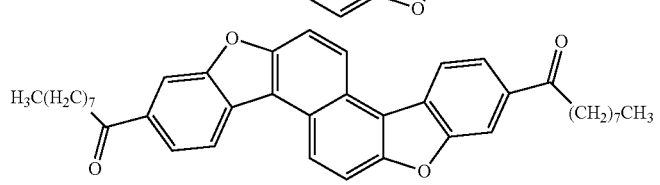
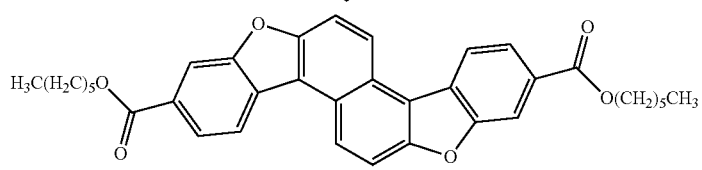

-continued
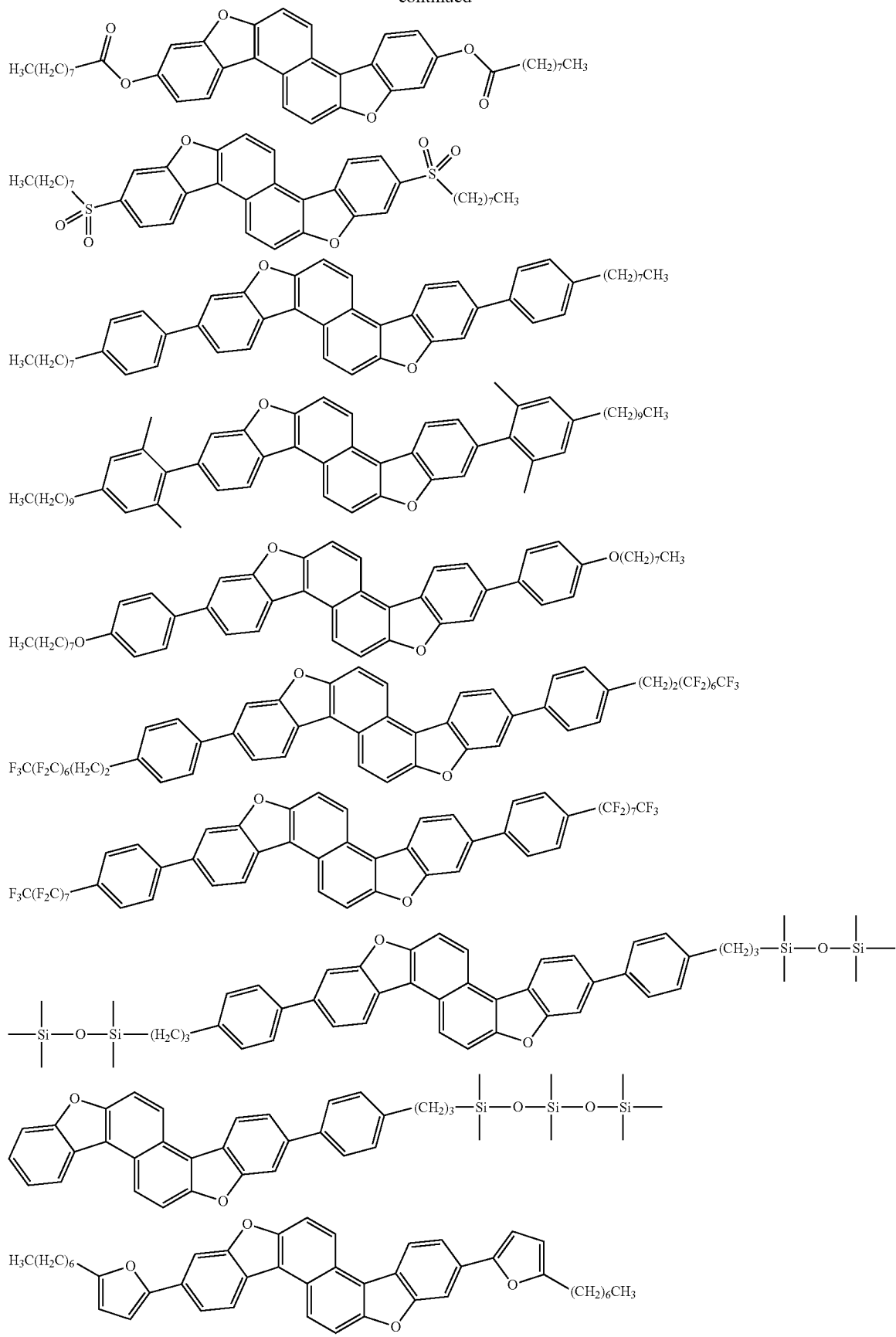

-continued
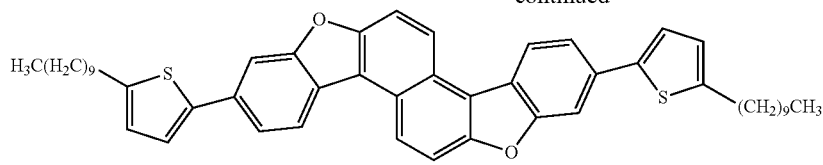
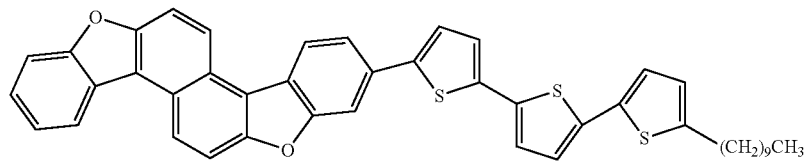
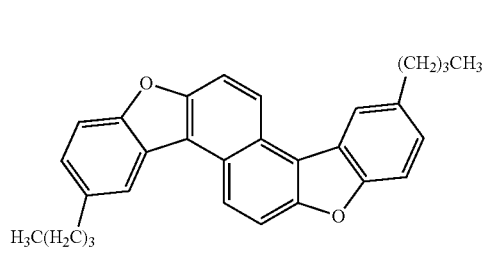
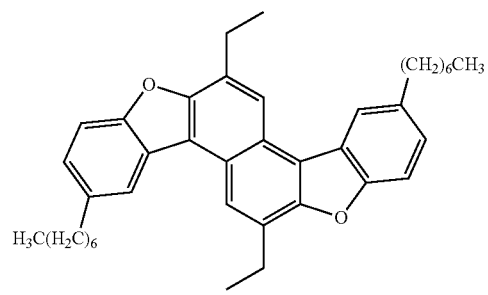
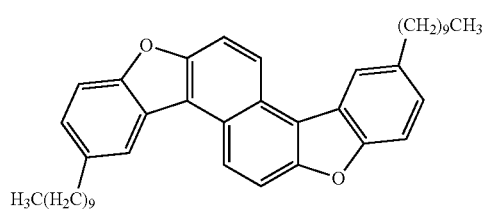
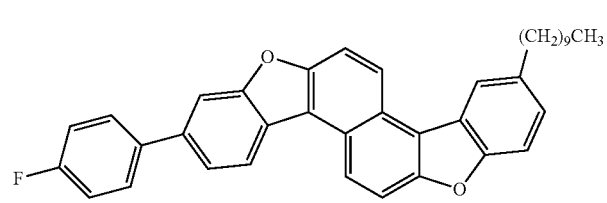
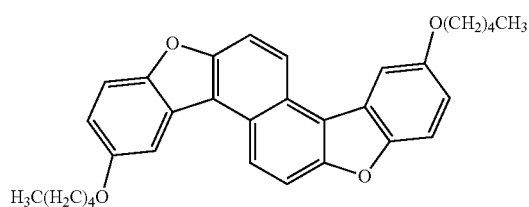
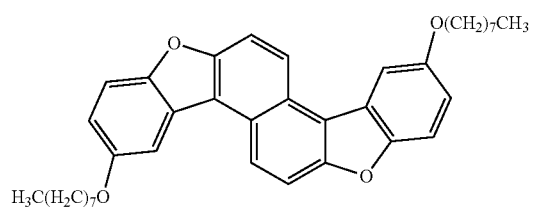
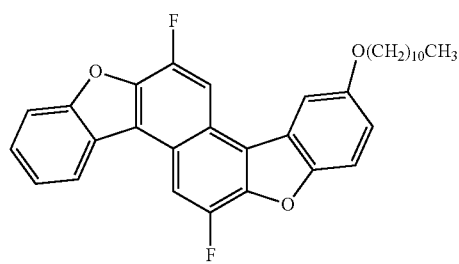
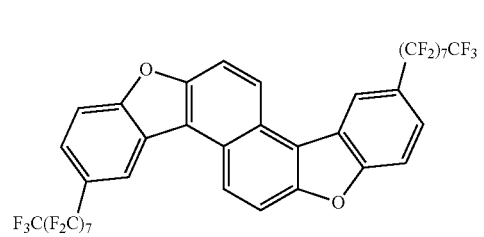
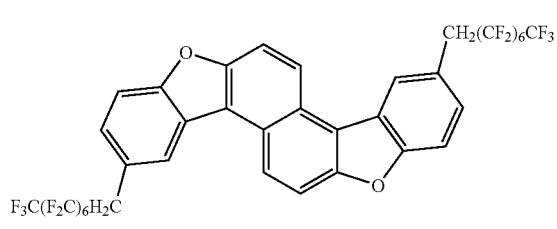
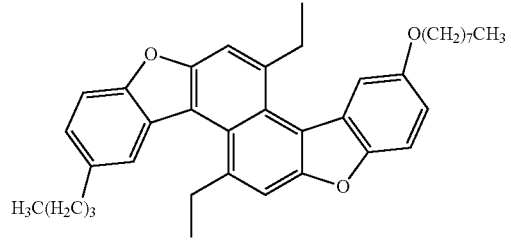

-continued
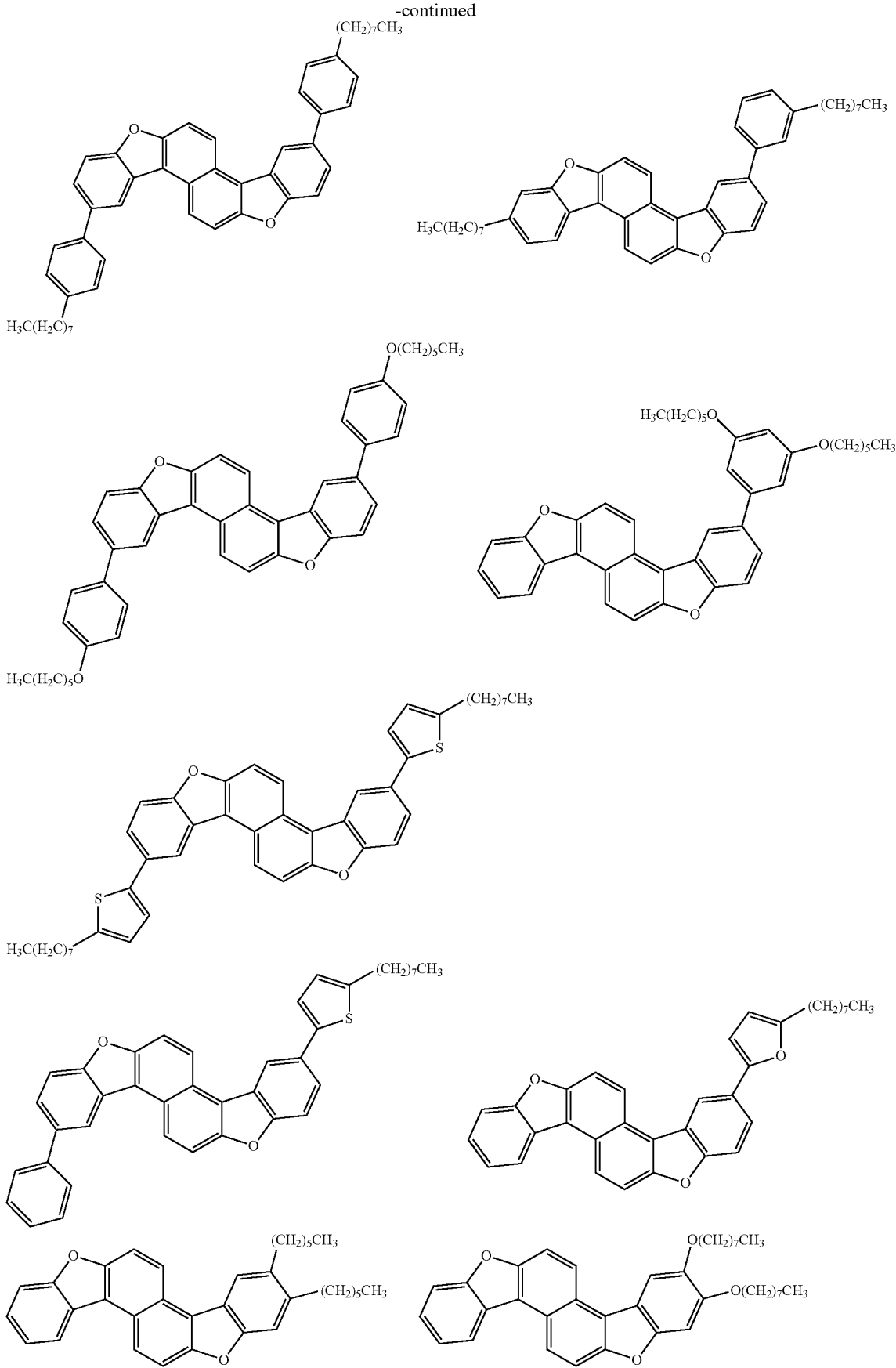

-continued

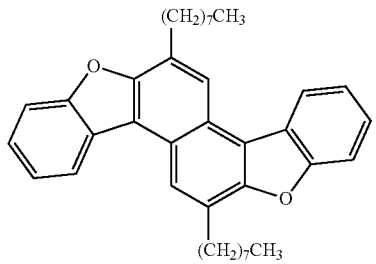
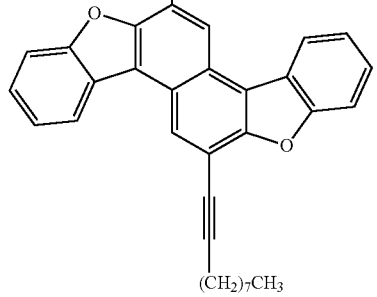

The compound represented by the formula (1) preferably has a molecular weight of 3,000 or less, more preferably 2,000 or less, further preferably 1,000 or less, and particularly preferably 850 or less. The molecular weight that is the upper limit or less is preferred since the compound has increased solubility in a solvent.

The molecular weight of the compound is preferably 400 or more, more preferably 450 or more, and further preferably 500 or more, from the standpoint of the stability of the film quality of the thin film.

The compound represented by the formula (1) may be synthesized by combining known reactions. For example, the compound may be synthesized with reference to JP-A-2010-59147 and the like.

In the reaction of forming a naphthobisbenzofuran ring in the invention, any reaction condition may be used. The reaction solvent used may be any solvent. An acid or a base is preferably used for promoting the ring-forming reaction, and particularly a base is preferably used. The optimum reaction condition may vary depending on the structure of the target naphthobisbenzofuran derivative, and may be determined with reference to the specific reaction shown in the aforementioned literature.

The synthesis intermediates having the various substituents may be synthesized by combining known reactions. The substituents may be introduced in any stage of the intermediates. The intermediates after synthesis is preferably purified by column chromatography, recrystallization or the like, and then purified by sublimation. The sublimation purification not only isolates organic impurities, but also effectively removes an inorganic salt, a residual solvent and the like.

Structure of Organic Thin Film Transistor

The organic thin film transistor of the invention contains the compound represented by the formula (1) in a semiconductor active layer.

The organic thin film transistor of the invention may further contain other layers in addition to the semiconductor active layer.

The organic thin film transistor of the invention is preferably used as an organic field effect transistor (FET), and is more preferably used as an insulated gate FET, in which the gate and the channel are insulated from each other.

Preferred embodiments of the organic thin film transistor of the invention will be described below with reference to the drawings, but the invention is not limited to the embodiments.

Laminated Structure

The laminated structure of the organic field effect transistor is not particularly limited, and various known structures may be used.

One example of the structure of the organic thin film transistor of the invention is a bottom-gate top-contact structure having a substrate as the lowermost layer having disposed thereon an electrode, an insulating layer, a semiconductor active layer (organic semiconductor layer), and two electrodes, in this order. In this structure, the electrode on the upper surface of the substrate as the lowermost layer is provided on apart of the substrate, and the insulating layer is disposed to be in contact with the substrate in the portion other than the electrode. The two electrodes disposed on the upper surface of the semiconductor active layer are disposed to be separated from each other.

A structure of a bottom-gate top-contact device is shown in FIG. 1. FIG. 1 is a schematic illustration showing a cross sectional structure of one example of the organic thin film transistor of the invention. The organic thin film transistor shown in FIG. 1 has a substrate 11 disposed as the lowermost layer, an electrode 12 disposed on a part of the upper surface of the substrate 11, and an insulating layer 13 is disposed to cover the electrode 12 and to be in contact with the substrate 11 in the portion other than the electrode 12. A semiconductor active layer 14 is provided on the upper surface of the insulating layer 13, and two electrodes 15a and 15b, which are separated from each other, are disposed on parts of the semiconductor active layer 14.

In the organic thin film transistor shown in FIG. 1, the electrode 12 is a gate, and the electrodes 15a and 15b each are a drain or a source. The organic thin film transistor shown in FIG. 1 is an insulated gate FET, in which the channel, which is an electric current path between the drain and the source, and the gate are insulated from each other.

Another example of the structure of the organic thin film transistor of the invention is a bottom-gate bottom-contact device.

Figure 2:
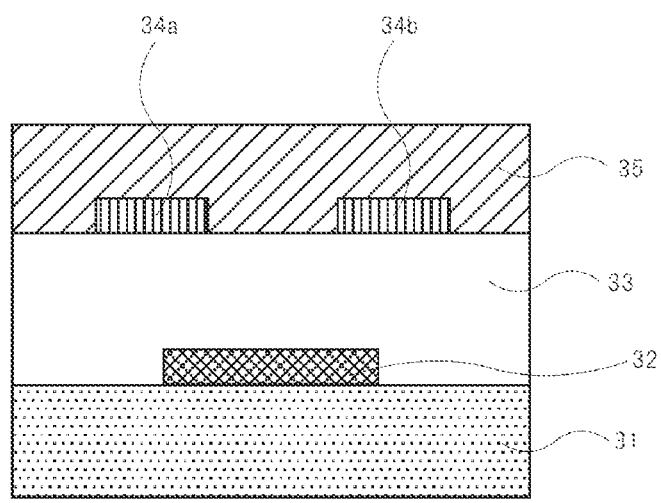
FIG. 2 is a schematic illustration showing a cross sectional structure of an organic thin film transistor that is produced as a substrate for measuring FET characteristics in the example of the invention.

A structure of a bottom-gate bottom-contact device is shown in FIG. 2. FIG. 2 is a schematic illustration showing a cross sectional structure of an organic thin film transistor that is produced as a substrate for measuring FET characteristics in the example of the invention. The organic thin film transistor shown in FIG. 2 has a substrate 31 disposed as the lowermost layer, an electrode 32 disposed on a part of the upper surface of the substrate 31, and an insulating layer 33 is disposed to cover the electrode 32 and to be in contact with the substrate 31 in the portion other than the electrode 32. A semiconductor active layer 35 is provided on the upper surface of the insulating layer 33, and two electrodes 34a and 34b are disposed under the semiconductor active layer 35.

In the organic thin film transistor shown in FIG. 2, the electrode 32 is a gate, and the electrodes 34a and 34b each are a drain or a source. The organic thin film transistor shown in FIG. 2 is an insulated gate FET, in which the channel, which is an electric current path between the drain and the source, and the gate are insulated from each other.

Other preferred examples of the structure of the organic thin film transistor of the invention include a top-gate top-contact device and a top-gate bottom-contact device, in which an insulator and a gate electrode are disposed on an organic semiconductor layer.

Thickness

The organic thin film transistor of the invention preferably has a total thickness of the transistor, for example, of from 0.1 to 0.5 μm, in the case where a thinner transistor is demanded.

Sealing

For shielding the organic thin film transistor device from the air and water to enhance the storage stability of the organic thin film transistor device, the entire organic thin film transistor device may be sealed with a metallic sealing canister, an inorganic material, such as glass and silicon nitride, a polymer material, such as parylene, a low molecular weight material, and the like.

Preferred embodiments of the layers of the organic thin film transistor of the invention will be described below, but the invention is not limited to the embodiments.

Substrate

Material

The organic thin film transistor of the invention preferably contains a substrate.

The material for the substrate is not particularly limited, and known materials may be used. Examples of the material include a polyester film, such as polyethylene naphthoate (PEN) and polyethylene terephthalate (PET), a cycloolefin polymer film, a polycarbonate film, a triacetyl cellulose (TAC) film, a polyimide film, these polymer films having an ultrathin glass layer laminated thereon, ceramics, silicone, quartz, glass, and the like, and silicone is preferred.

Electrode

Material

The organic thin film transistor of the invention preferably contains an electrode.

Examples of the material for the electrode include known electroconductive materials, for example, a metal material, such as Cr, Al, Ta, Mo, Nb, Cu, Ag, Au, Pt, Pd, In, Ni and Nd, an alloy material of the metal materials, a carbon material, and an electroconductive polymer, which may be used without particular limitation.

Thickness

The thickness of the electrode is not particularly limited and is preferably from 10 to 50 nm.

The gate width (or the channel width) W and the gate length (or the channel length) L are not particularly limited, and the ratio W/L is preferably 10 or more, and more preferably 20 or more.

Insulating Layer

Material

The material for the insulating layer is not particularly limited as far as the necessary insulating effect is obtained, and examples thereof include silicon dioxide, silicon nitride, a fluorine polymer insulating material, such as PTFE and CYTOP, a polyester insulating material, a polycarbonate insulating material, an acrylic polymer insulating material, an epoxy resin insulating material, a polyimide insulating material, a polyvinylphenol resin insulating material, and a poly-p-xylene resin insulating material.

The upper surface of the insulating layer may be surface-treated, and preferred examples thereof used include an insulating layer formed of silicon dioxide, the surface of which is surface-treated by coating hexamethyldisilazane (HMDS) or octadecyltrichlorosilane (OTS) thereon.

Thickness

The thickness of the insulating layer is not particularly limited, and in the case where a thin insulating layer is demanded, the thickness thereof is preferably from 10 to 400 nm, more preferably from 20 to 200 nm, and particularly preferably from 50 to 200 nm.

Semiconductor Active Layer

Material

The organic thin film transistor of the invention contains the compound represented by the formula (1), i.e., the compound of the invention, in the semiconductor active layer.

The semiconductor active layer may be a layer that is formed of the compound of the invention, or a layer containing a polymer binder described later in addition to the compound of the invention. The semiconductor active layer may contain a residual solvent used on forming the film.

The content of the polymer binder in the semiconductor active layer is not particularly limited, and the polymer binder is preferably used in a range of from 0 to 95% by mass, more preferably used in a range of from 10 to 90% by mass, further preferably used in a range of from 20 to 80% by mass, and particularly preferably used in a range of from 30 to 70% by mass.

Thickness

The thickness of the semiconductor active layer is not particularly limited, and in the case where a thin semiconductor active layer is demanded, the thickness thereof is preferably from 10 to 400 nm, more preferably from 10 to 200 nm, and particularly preferably from 10 to 100 nm.

Organic Semiconductor Material for Non-Light Emitting Organic Semiconductor Device The invention also relates to an organic semiconductor material for a non-light emitting organic semiconductor device containing the compound represented by the formula (1), i.e., the compound of the invention.

Non-Light Emitting Organic Semiconductor Device

The non-light emitting organic semiconductor device referred herein means a device that is not intended to emit light. The non-light emitting organic semiconductor device is preferably a non-light emitting organic semiconductor device that uses an electronic element having a layer structure of thin films. The non-light emitting organic semiconductor device encompasses an organic thin film transistor, an organic photoelectric conversion device (such as a solid state imaging device for a photosensor, and a solar cell for energy conversion), a gas sensor, an organic rectifying device, an organic inverter, an information recording device, and the like. The organic photoelectric conversion device maybe used for both a photosensor (i.e., a solid state imaging device) and energy conversion (i.e., a solar cell). Preferred examples of the device include an organic photoelectric conversion device and an organic thin film transistor, and more preferred examples thereof include an organic thin film transistor. Accordingly, the organic semiconductor material for a non-light emitting organic semiconductor device of the invention is preferably a material for an organic thin film transistor as described above.

Organic Semiconductor Material

The organic semiconductor material referred herein means an organic material that shows characteristics of a semiconductor. The organic semiconductor material includes a p-type (hole transporting) organic semiconductor, which shows conductivity with holes as a carrier, and an n-type (electron transporting) organic semiconductor, which shows conductivity with electrons as a carrier, as similar to a semiconductor material formed of an inorganic material.

The compound of the invention may be used as any of a p-type organic semiconductor material and an n-type organic semiconductor material, and is preferably used as a p-type organic semiconductor material. The flowability of a carrier in an organic semiconductor is shown by a carrier mobility μ. The carrier mobility μ is preferably as large as possible, and is preferably $5 \times 10^{-4}$ cm$^2$/Vs or more, more preferably $1 \times 10^{-3}$ cm$^2$/Vs or more, further preferably $5 \times 10^{-3}$ cm$^2$/Vs or more, and particularly preferably $10^{-2}$ cm$^2$/Vs or more. The carrier mobility μ may be obtained from the characteristics of a field effect transistor (FET) device produced or by a time-of-flight (TOF) measurement method.

Organic Semiconductor Thin Film for Non-Light Emitting Organic Semiconductor Device Material The invention also relates to an organic semiconductor thin film for a non-light emitting organic semiconductor device containing the compound represented by the formula (1), i.e., the compound of the invention.

The organic semiconductor thin film for a non-light emitting organic semiconductor device of the invention contains the compound represented by the formula (1), i.e., the compound of the invention, and an embodiment thereof that contains no polymer binder is also preferred.

The organic semiconductor thin film for a non-light emitting organic semiconductor device of the invention may contain the compound represented by the formula (1), i.e., the compound of the invention, and a polymer binder.

Examples of the polymer binder include an insulating polymer, such as polystyrene, polycarbonate, polyarylate, polyester, polyamide, polyimide, polyurethane, polysiloxane, polysulfone, polymethyl methacrylate, polymethyl acrylate, cellulose, polyethylene and polypropylene, copolymers thereof, a photoconductive polymer, such as polyvinylcarbazole and polysilane, and an electroconductive polymer and a semiconductor polymer, such as polythiophene, polypyrrole, polyaniline and poly-p-phenylenevinylene.

The polymer binder maybe used solely or as a combination of plural kinds thereof.

The organic semiconductor material and the polymer binder may be uniformly mixed, or a part or the whole thereof may be phase-separated, and from the standpoint of the charge mobility, such a structure that the organic semiconductor and the binder are phase-separated in the thickness direction in the film is most preferred since the charge migration of the organic semiconductor may not be inhibited by the binder.

Taking the mechanical strength of the thin film into consideration, a polymer binder having a high glass transition temperature is preferred, and taking the charge mobility into consideration, a polymer binder having a structure that contains no polar group, a photoconductive polymer, and an electroconductive polymer are preferred.

The amount of the polymer binder used is not particularly limited, and the polymer binder maybe preferably used in a range of from 0 to 95% by mass, more preferably used in a range of from 10 to 90% by mass, further preferably used in a range of from 20 to 80% by mass, and particularly preferably used in a range of from 30 to 70% by mass, in the organic semiconductor thin film for a non-light emitting organic semiconductor device of the invention.

In the invention, an organic thin film having good film quality may be obtained by using the compound having the aforementioned structure. Specifically, the compound of the invention has good crystallinity to enable formation of a film having a sufficient thickness, and thus the organic semiconductor thin film for a non-light emitting organic semiconductor device of the invention thus obtained may have good quality.

Film Forming Method

The compound of the invention may be formed as a film on a substrate by any method.

On forming the film, the substrate may be heated or cooled, and the film quality and the molecular packing in the film may be controlled by changing the temperature of the substrate. The temperature of the substrate is not particularly limited, and is preferably in a range of from 0 to 200° C.

On forming a film of the compound of the invention on a substrate, the film may be formed by a vacuum process or a solution process, both of which are preferred.

Specific examples of the film formation by a vacuum process include a physical vapor phase growing method, such as a vacuum vapor deposition method, a sputtering method, an ion plating method and a molecular epitaxy (MBE) method, and a chemical vapor deposition (CVD) method, such as plasma polymerization, and a vacuum vapor deposition method is preferably used.

The film formation by a solution process means a method, in which an organic compound is dissolved in a solvent capable of dissolving the same, and a film is formed by using the resulting solution. Specific examples thereof used include ordinary methods, for example, a coating method, such as a casting method, a dip coating method, a die coater method, a roll coater method, a bar coater method and a spin coating method, a printing method, such as an ink-jet method, a screen printing method, a gravure printing method, a flexography printing method, an offset printing method and a microcontact printing method, and a Langmuir-Blodgett (LB) method, and a casting method, a spin coating method, an ink-jet method, a gravure printing method, a flexography printing method, an offset printing method and a microcontact printing method are particularly preferably used.

The organic semiconductor thin film for a non-light emitting organic semiconductor device of the invention is preferably produced by a solution coating method. In the case where the organic semiconductor thin film for a non-light emitting organic semiconductor device of the invention contains a polymer binder, the thin film is preferably formed such a method that the material for forming the layer and the polymer binder are dissolved or dispersed in a suitable solvent to prepare a coating liquid, which is then coated by various coating methods to form the thin film.

The coating solution for a non-light emitting organic semiconductor device of the invention capable of being used for film formation by a solution process will be described below.

Coating Solution for Non-Light Emitting Organic Semiconductor Device

The invention also relates to a coating solution for a non-light emitting organic semiconductor device containing the compound represented by the formula (1), i.e., the compound of the invention.

In the case where the film is formed on a substrate by a solution process, the material for forming the film may be dissolved or dispersed in a suitable organic solvent (for example, a hydrocarbon solvent, such as hexane, octane, decane, toluene, xylene, mesitylene, ethylbenzene, decalin and 1-methylnaphthalene, a ketone solvent, such as acetone, methyl ethyl ketone, methyl isobutyl ketone and cyclohexanone, a halogenated hydrocarbon solvent, such as dichloromethane, chloroform, tetrachloromethane, dichloroethane, trichloroethane, tetrachloroethane, chlorobenzene, dichlorobenzene and chlorotoluene, an ester solvent, such as ethyl acetate, butyl acetate and amyl acetate, an alcohol solvent, such as methanol, propanol, butanol, pentanol, hexanol, cyclohexanol, methyl cellosolve, ethyl cellosolve and ethylene glycol, an ether solvent, such as dibutyl ether, tetrahydrofuran, dioxane and anisole, an amide or imide solvent, such as N,N-dimethylformamide, N,N-dimethylacetamide, 1-methyl-2-pyrrolidone and 1-methyl-2-imidazolidinone, a sulfoxide solvent, such as dimethylsulfoxide, and a nitrile solvent, such as acetonitrile) and/or water to prepare a coating liquid, which may be then coated by various coating methods to form the thin film. The solvent may be used solely or as a combination of plural kinds thereof. The concentration of the compound represented by the formula (1) in the coating liquid is preferably from 0.1 to 80% by mass, and more preferably from 0.1 to 10% by mass, by which a film having an arbitrary thickness may be formed.

For forming a film by a solution process, it is necessary to dissolve the materials in the aforementioned solvent, but it is insufficient that the materials are simply dissolved in the solvent. In general, a material to be formed into a film by a vacuum process may be dissolved in a solvent in a certain extent. However, the solution process includes a step of evaporating the solvent to form a thin film, after coating the materials dissolved in a solvent, and most of materials that are not suitable for forming a film by a solution process have high crystallinity, and thus may be disadvantageously crystallized (agglomerated) in the step to fail to provide a favorable thin film. The compound represented by the formula (1) is advantageous also in such a point that the compound may not cause the disadvantageous crystallization (agglomeration).

As the coating solution for a non-light emitting organic semiconductor device of the invention, such an embodiment is also preferred that contains the compound represented by the formula (1), i.e., the compound of the invention, and contains no polymer binder.

The coating solution for a non-light emitting organic semiconductor device of the invention may contain the compound represented by the formula (1), i.e., the compound of the invention, and a polymer binder. In this case, the thin film may be formed in such a manner that the material for forming the layer and the polymer binder are dissolved or dispersed in the suitable solvent described above to prepare a coating liquid, which is then coated by various coating method to form the thin film. The polymer binder may be selected from those described above.

EXAMPLES

The features of the invention will be described more specifically with reference to examples and comparative examples below. The materials, the amounts used, the ratios, the contents of processes, the procedures of processes, and the like shown in the examples may be appropriately changed unless they deviate the substance of the invention. Accordingly, the scope of the invention is not construed as being limited to the following examples.

Synthesis Example

Synthesis of Compound 1

A compound 1 was synthesized according to the following scheme.

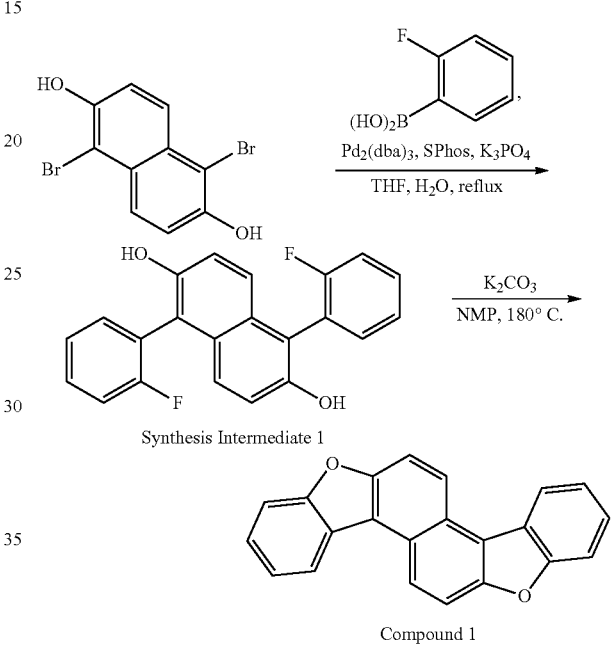

3.18 g (10.0 mmol) of 1,5-dibromo-2,6-dihydroxynaphthalene, 7.00 g (50.0 mmol) of 2-fluorophenylboronic acid, 458 mg (0.50 mmol) of tris(dibenzylideneacetone)dipalladium, 820 mg (2.00 mmol) of 2-dicyclohexylphosphino-2',6'-dimethoxybiphenyl, 8.49 g (40.0 mmol) of potassium phosphate, 35 mL of THF, and 17.5 mL of water were mixed and refluxed under heating in a nitrogen atmosphere for 2 hours. The reaction liquid was cooled to room temperature, to which ethyl acetate and water were then added, and the organic layer was extracted. The organic layer was concentrated, then purified by silica gel column chromatography (toluene/ethyl acetate=9/1), and further rinsed out with methanol, thereby providing 2.0 g of a synthesis intermediate 1 as a white solid matter (yield: 57%).

1.74 g (5.00 mmol) of the synthesis intermediate 1, 1.66 g (12.0 mmol) of potassium carbonate, and 25 mL of N-methyl-2-pyrrolidone were mixed and heated to 180° C. in a nitrogen atmosphere for 2 hours. The reaction liquid was cooled to room temperature, to which pure water was then added, and a solid matter thus deposited was rinsed sequentially with pure water and ethanol. The solid matter was then recrystallized from toluene/methanol (3/1), thereby providing 1.42 g of the compound 1 as a white solid matter (yield: 92%).

$^1$H NMR (400 MHz, in CDCl$_3$); δ=8.78 (d, 2H), 8.49 (d, 2H), 8.03 (d, 2H), 7.75 (d, 2H), 7.58-7.50 (m, 4H) ppm Synthesis of Compounds 2 to 19
Compounds 2 to 19 were synthesized in the similar manner as in the compound 1.
The structures of the compounds 1 to 19 are shown below.
Compound 1
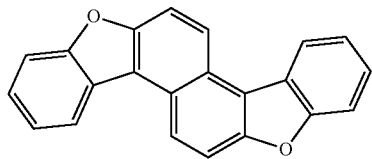
Compound 2
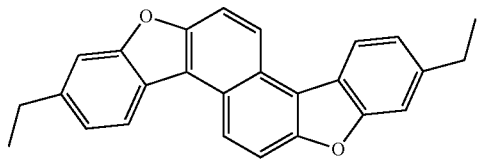
Compound 3
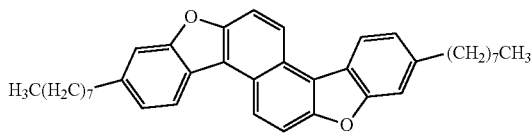
Compound 4
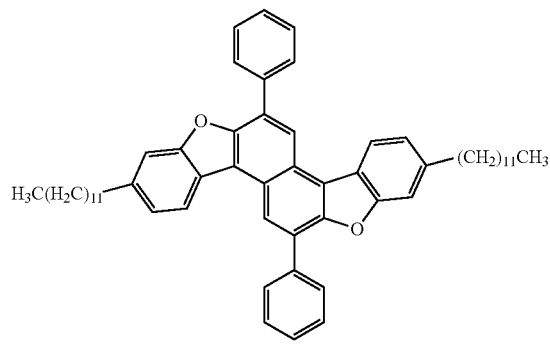
Compound 5
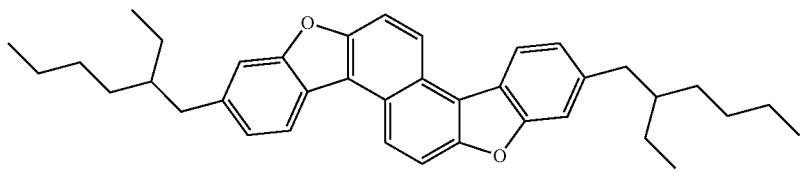
Compound 6
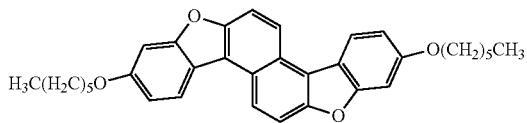
Compound 7
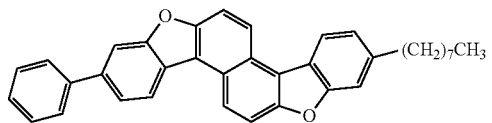
Compound 8
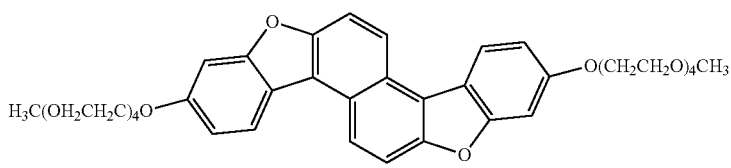
Compound 9
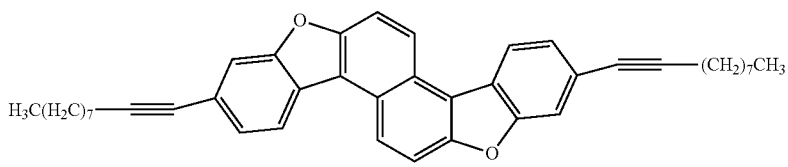
Compound 10
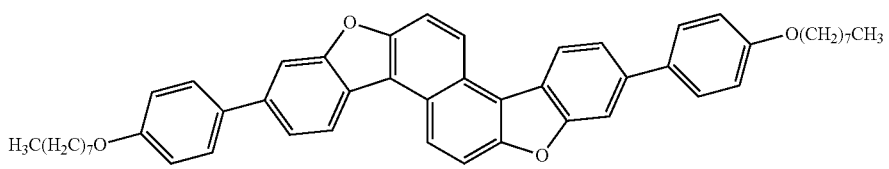

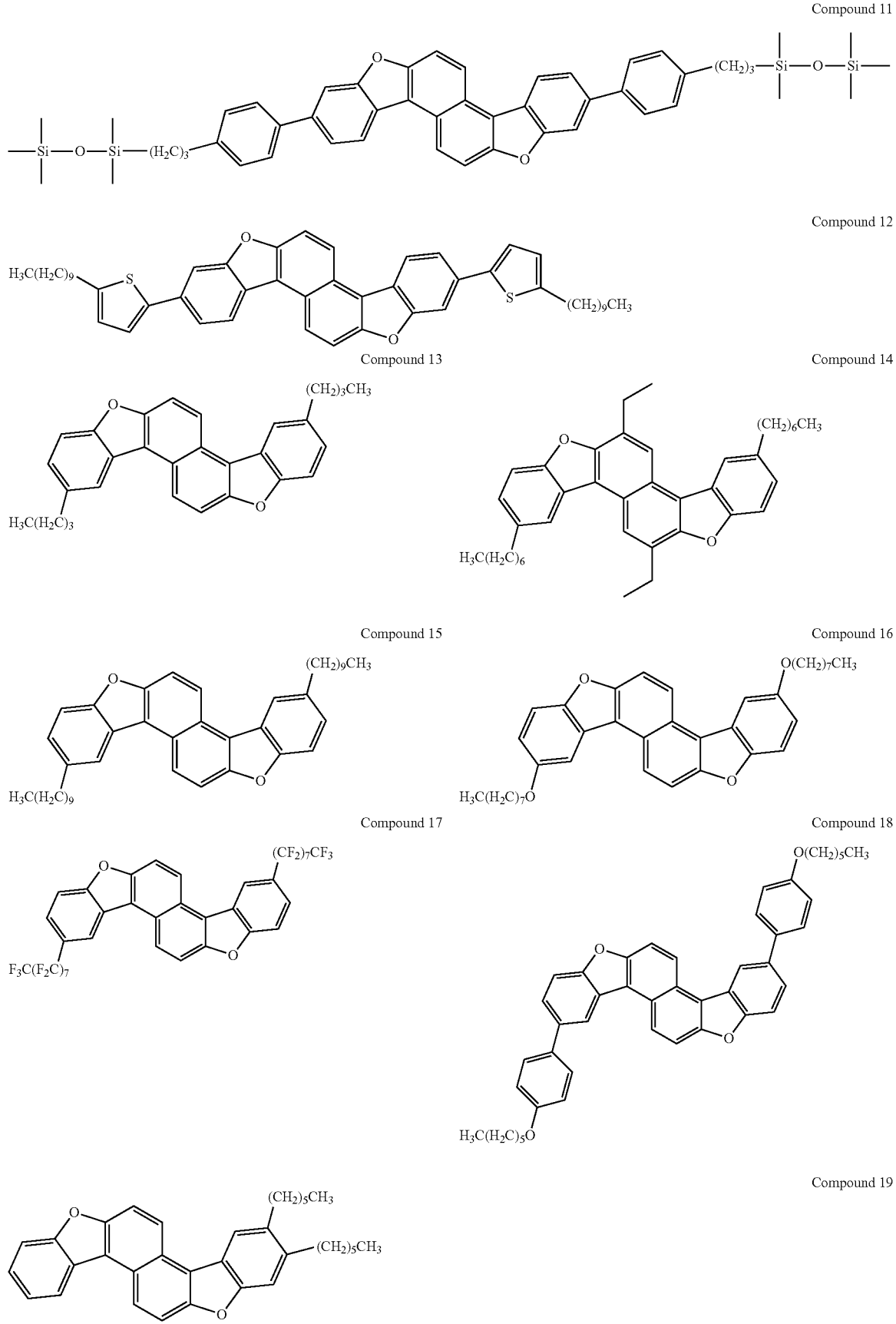

The structures of comparative compounds 1 to 7 used in a semiconductor active layer (i.e., an organic semiconductor layer) of comparative devices are shown below.

The comparative compound 1 is described as the compound 241 in JP-A-2010-059147, and the NMR data of the compound is described in Table 4 of the literature.

The comparative compound 2 is described as the compound 260 in JP-A-2010-059147, the NMR data of the compound is described in Table 4 of the literature, and an example using the compound as a dopant of a light emitting layer of an organic electroluminescent device is described in Example 5 of the literature.

The comparative compound 3 is described as the compound 265 in JP-A-2010-059147, and the NMR data of the compound is described in Table 4 of the literature.

The comparative compound 4 is described as the compound 19 in JP-A-2010-059147, the NMR data of the compound is described in Table 1 of the literature, an example using the compound as a dopant of a light emitting layer of an organic electroluminescent device is described in Example 4 of the literature, and an example using the compound as a material for a hole transporting layer of an organic electroluminescent device is described in Example 5 of the literature.

The comparative compound 5 is described as the example compound 101 in JP-A-2009-267134, and an example using the compound in an organic semiconductor layer of an organic transistor is described in Example 12 of the literature.

The comparative compound 6 is described as the example compound 103 in JP-A-2009-267134, and an example using the compound in an organic semiconductor layer of an organic transistor is described in Example 13 of the literature.

The comparative compound 7 is described as the synthesis example of the compound No. 1 in Example 1 of JP-A-2012-513459, and an example using the compound as a material for a solar cell is described in Example 11 of the literature.

Comparative Compound 1

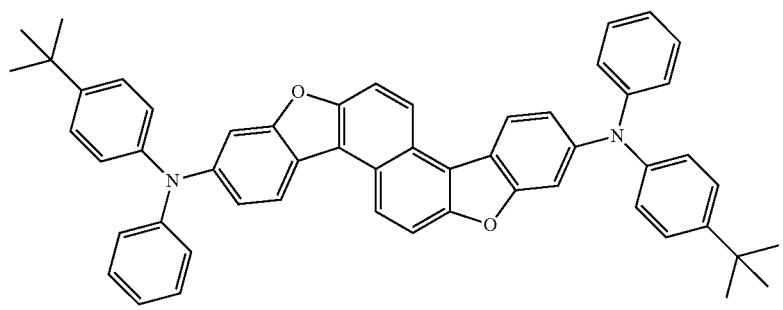

Comparative Compound 2

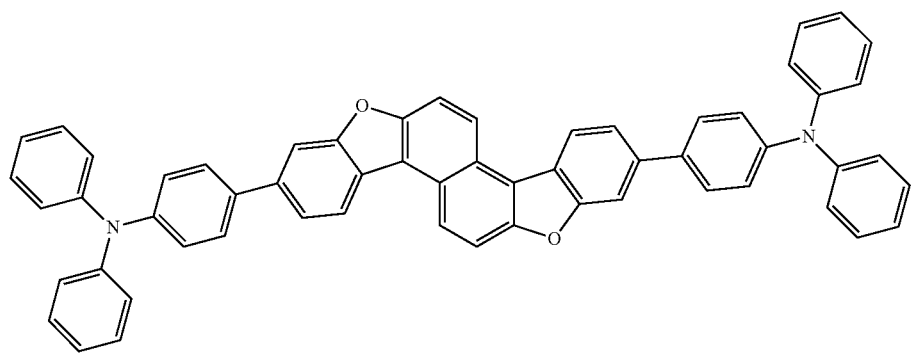

Comparative Compound 3

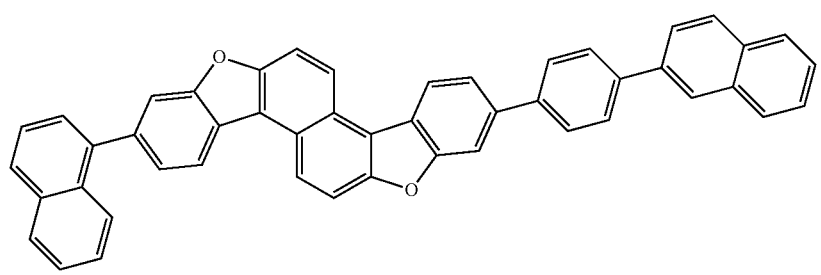

Comparative Compound 4

Comparative Compound 5

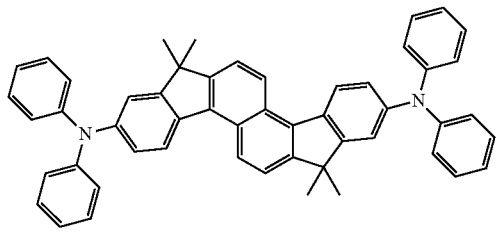

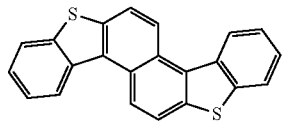

Comparative Compound 6

Comparative Compound 7

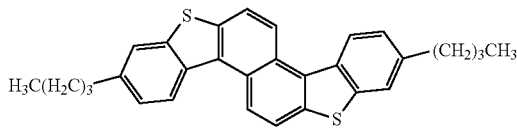

Production and Evaluation of Devices

All the materials used for producing devices were purified by sublimation, and were confirmed to have a purity (absorption intensity area ratio at 254 nm) of 99.95% or more by high-performance liquid chromatography (TSKgel ODS-100Z, available from Tosoh Corporation).

Example 1

Formation of Semiconductor Active Layer (Organic Semiconductor Layer) Only with Compound The compound of the invention or the comparative compound (1 mg each) and 1,2-dichlorobenzene (1 mL) were mixed and heated to 100° C. to prepare a coating solution for a non-light emitting organic semiconductor device. The coating solution was cast on a substrate for measuring FET characteristics heated to 100° C. to form an organic semiconductor thin film for a non-light emitting organic semiconductor device, thereby providing an organic thin film transistor device of Example 1 for measuring FET characteristics. The substrate for measuring FET characteristics used was a silicon substrate having a bottom-contact structure having chromium/gold electrodes (gate width W=100,000 μm, gate length L=100 μm) disposed in an interdigitated form as source and drain electrodes, and $SiO_2$ (thickness: 200 nm) as an insulating film (the schematic structural illustration shown in FIG. 2).

The FET characteristics of the organic thin film transistor device of Example 1 were evaluated in terms of the carrier mobility and the fluctuation of the threshold voltage after repeated driving by using a semiconductor parameter analyzer (4156C, produced by Agilent Technologies, Inc.) having a semi-automatic prober (AX-2000, produced by Vector Semiconductor Co., Ltd.) connected thereto under a normal pressure nitrogen atmosphere.

The results obtained are shown in Table 1 below.

(a) Carrier Mobility

While applying a voltage of −100 V between the source electrode and the drain electrode of the organic thin film transistor device (FET device), the gate voltage was changed within a range of from 20 to −100 V, and the carrier mobility μ was calculated by the following expression showing the drain current $I_d$.

$$I_d=(W/2L)\mu C_i(V_g-V_{th})^2$$

wherein L represents the gate length, W represents the gate width, $C_i$ represents the capacity of the insulating layer per unit area, $V_g$ represents the gate voltage, and $V_{th}$ represents the threshold voltage. A device that exhibited a carrier mobility of less than $1\times10^{-5}$ cm²/Vs was not subjected to the subsequent evaluation of (b) the fluctuation of the threshold voltage after repeated driving due to the too poor property thereof.

(b) Fluctuation of Threshold Voltage after Repeated Driving

While applying a voltage of −100 V between the source electrode and the drain electrode of the organic thin film transistor device (FET device), the gate voltage was changed 100 times within a range of from 20 to −100 V, and the same measurement as in the measurement (a) above to evaluate the difference ($|V_1-V_0|$) between the threshold voltage $V_0$ before repeated driving and the threshold voltage $V_1$ after repeated driving according to the following three grades. A smaller value thereof shows higher repeated driving stability of the device and thus is preferred.

| | |
|---|---|
| $\|V_1-V_0\|\geq 5$ V | A: |
| 5 V<$\|V_1-V_0\|\geq 10$ V | B: |
| $\|V_1-V_0\|>10$ V | C: |

TABLE 1

| Device No. | Organic semiconductor material | Carrier mobility (cm²/Vs) | Fluctuation of threshold voltage after repeated driving | Note |
|---|---|---|---|---|
| Device 1 | Compound 3 | $1 \times 10^{-2}$ | A | invention |
| Device 2 | Compound 4 | $3 \times 10^{-3}$ | A | invention |
| Device 3 | Compound 5 | $2 \times 10^{-3}$ | A | invention |
| Device 4 | Compound 6 | $9 \times 10^{-3}$ | A | invention |
| Device 5 | Compound 7 | $8 \times 10^{-3}$ | A | invention |
| Device 6 | Compound 8 | $3 \times 10^{-3}$ | A | invention |
| Device 7 | Compound 11 | $4 \times 10^{-3}$ | A | invention |
| Device 8 | Compound 12 | $9 \times 10^{-3}$ | A | invention |
| Device 9 | Compound 13 | $5 \times 10^{-3}$ | A | invention |
| Device 10 | Compound 14 | $1 \times 10^{-3}$ | A | invention |
| Device 11 | Compound 15 | $7 \times 10^{-3}$ | A | invention |
| Device 12 | Compound 16 | $8 \times 10^{-3}$ | A | invention |
| Device 13 | Compound 18 | $3 \times 10^{-3}$ | A | invention |
| Device 14 | Compound 19 | $1 \times 10^{-3}$ | A | invention |
| Comparative Device 1 | Comparative Compound 1 | $<1 \times 10^{-5}$ | — | comparison |
| Comparative Device 2 | Comparative Compound 2 | $<1 \times 10^{-5}$ | — | comparison |

TABLE 1-continued

| Device No. | Organic semiconductor material | Carrier mobility (cm$^2$/Vs) | Fluctuation of threshold voltage after repeated driving | Note |
|---|---|---|---|---|
| Comparative Device 3 | Comparative Compound 3 | <1 × 10$^{-5}$ | — | comparison |
| Comparative Device 4 | Comparative Compound 4 | <1 × 10$^{-5}$ | — | comparison |
| Comparative Device 5 | Comparative Compound 5 | 3 × 10$^{-5}$ | C | comparison |
| Comparative Device 6 | Comparative Compound 6 | 1 × 10$^{-4}$ | C | comparison |
| Comparative Device 7 | Comparative Compound 7 | <1 × 10$^{-5}$ | — | comparison |

It was understood from Table 1 that the organic thin film transistor devices using the compounds of the invention had a high carrier mobility and a small fluctuation of the threshold voltage after repeated driving. Accordingly, it was understood that the compound of the invention was favorably used as an organic semiconductor material for a non-light emitting organic semiconductor device.

On the other hand, the organic thin film transistor devices using the comparative compounds 1 to 4 and 7 had a low carrier mobility. The organic thin film transistor devices using the comparative compounds 5 and 6 had a large fluctuation of the threshold voltage after repeated driving.

Example 2

Formation of Semiconductor Active Layer (Organic Semiconductor Layer) with both Compound and Binder Organic thin film transistor devices for measuring FET characteristics were produced in the same manner as in Example 1 except for using a coating solution prepared in such a manner that the compound of the invention or the comparative compound (0.5 mg each), 0.5 mg of PaMS (poly(α-methylstyrene), produced by Sigma-Aldrich, Inc.) and 1,2-dichlorobenzene (1 mL) were mixed and heated to 100° C., and then evaluated in the same manner as in Example 1.

The results obtained are shown in Table 1 below.

TABLE 2

| Device No. | Organic semiconductor material | Carrier mobility (cm$^2$/Vs) | Fluctuation of threshold voltage after repeated driving | Note |
|---|---|---|---|---|
| Device 15 | Compound 1 | 9 × 10$^{-4}$ | A | invention |
| Device 16 | Compound 2 | 1 × 10$^{-3}$ | A | invention |
| Device 17 | Compound 3 | 6 × 10$^{-3}$ | A | invention |
| Device 18 | Compound 9 | 4 × 10$^{-3}$ | A | invention |
| Device 19 | Compound 10 | 5 × 10$^{-3}$ | A | invention |
| Device 20 | Compound 11 | 3 × 10$^{-3}$ | A | invention |
| Device 21 | Compound 17 | 4 × 10$^{-3}$ | A | invention |
| Comparative Device 8 | Comparative Compound 1 | <1 × 10$^{-5}$ | — | comparison |
| Comparative Device 9 | Comparative Compound 3 | <1 × 10$^{-5}$ | — | comparison |
| Comparative Device 10 | Comparative Compound 5 | <1 × 10$^{-5}$ | — | comparison |
| Comparative Device 11 | Comparative Compound 6 | 2 × 10$^{-5}$ | C | comparison |
| Comparative Device 12 | Comparative Compound 7 | <1 × 10$^{-5}$ | — | comparison |

It was understood from Table 2 that the organic thin film transistor devices having a semiconductor active layer formed by using the compounds of the invention along with the binder had a high carrier mobility and a small fluctuation of the threshold voltage after repeated driving. Accordingly, it was understood that the compound of the invention was favorably used as an organic semiconductor material for a non-light emitting organic semiconductor device.

On the other hand, the organic thin film transistor devices having a semiconductor active layer formed by using the comparative compounds 1, 3, 5 and 7 along with the binder had a low carrier mobility. The organic thin film transistor device having a semiconductor active layer formed by using the comparative compound 6 along with the binder had a large fluctuation of the threshold voltage after repeated driving.

It was understood from the visual observation and the observation with an optical microscope of the organic thin film transistor devices obtained in Example 2 that the thin films using PaMS as a binder all had considerably high smoothness and uniformity of the film.

It was understood from these results that the comparative devices having a semiconductor active layer formed with the composite system of the binder and the comparative compound had a considerably low carrier mobility, whereas the organic thin film transistor devices of the invention having a semiconductor active layer formed with both the compound of the invention and the binder had a good carrier mobility, a small fluctuation of the threshold voltage after repeated driving, and considerably high smoothness and uniformity of the film.

While the present invention has been described in detail and with reference to specific embodiments thereof, it will be apparent to one skilled in the art that various changes and modifications can be made therein without departing from the spirit and scope thereof.

The present disclosure relates to the subject matter contained in International Application No. PCT/JP2013/077020, filed on Oct. 4, 2013, and Japanese Patent Application No. 2012-227654 filed on Oct. 15, 2012, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims.

REFERENCE SIGN LIST

11 substrate
12 electrode
13 insulating layer
14 semiconductor active layer (organic material layer or organic semiconductor layer)
15a, 15b electrode
31 substrate
32 electrode
33 insulating layer
34a, 34b electrode
35 semiconductor active layer (organic material layer or organic semiconductor layer)

What is claimed is:

1. An organic thin film transistor containing a compound represented by the following formula (1) in a semiconductor active layer:

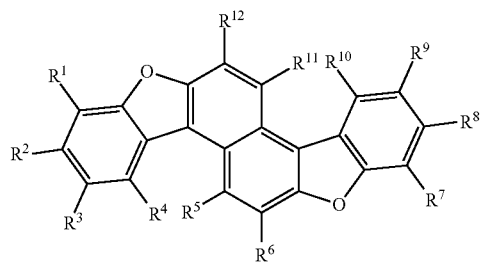

Formula (1)

wherein $R^1$ to $R^{12}$ each independently represent a hydrogen atom or a substituent, provided that at least one of $R^1$ to $R^{12}$ represents a substituent represented by the following formula (W), or all of $R^1$ to $R^{12}$ represent a hydrogen atom:

\*-L-R   Formula (W)

wherein * represents a position bonded to the naphthobisbenzofuran skeleton; L represents a single bond, a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group having 6 to 12 carbon atoms, an oligoethyleneoxy group having a repeating number of an ethyleneoxy unit of 2 or more, or an oligosiloxane group having 2 or more silicon atoms:

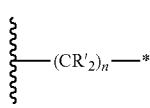 (L-1)

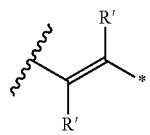 (L-2)

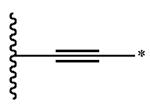 (L-3)

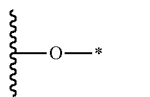 (L-4)

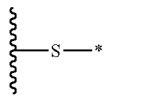 (L-5)

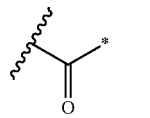 (L-6)

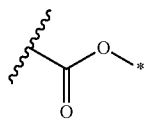 (L-7)

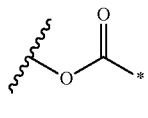 (L-8)

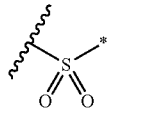 (L-9)

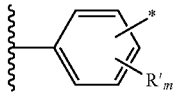 (L-10)

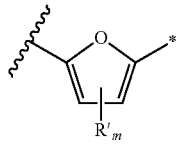 (L-11)

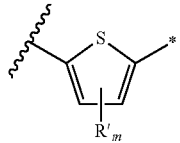 (L-12)

wherein in the formulae (L-1) to (L-12), the wavy line represents a position bonded to the naphthobisbenzofuran skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-2), (L-10), (L-11) and (L-12), R' each independently represent a hydrogen atom or a substituent.

2. The organic thin film transistor according to claim 1, wherein at least one of $R^2$, $R^3$, $R^8$ and $R^9$ represents a substituent represented by the formula (W).

3. The organic thin film transistor according to claim 1, wherein the compound represented by the formula (1) is a compound represented by the following formula (2-1) or (2-2):

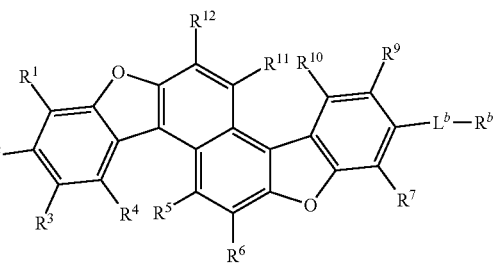

Formula (2-1)

wherein $R^1$, $R^3$ to $R^7$, and $R^9$ to $R^{12}$ each independently represent a hydrogen atom or a substituent; $L^a$ and $L^b$ each independently represent a single bond, a divalent linking group represented by any one of the following formulae (L-1) to (L-12), or a divalent linking group containing 2 or more divalent linking groups each represented by any one of the following formulae (L-1) to (L-12) bonded to each other; and $R^a$ and $R^b$ each independently represent a substituted or unsubstituted alkyl group having 6 to 12 carbon atoms, an oligoethyleneoxy group having a repeating number of an ethyleneoxy unit of 2 or more, or an oligosiloxane group having 2 or more silicon atoms, Formula (2-2)

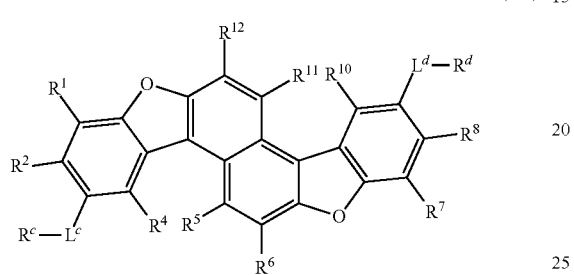

wherein $R^1$, $R^2$, $R^4$ to $R^8$, and $R^{10}$ to $R^{12}$ each independently represent a hydrogen atom or a substituent; $L^c$ and $L^d$ each independently represent a single bond, a divalent linking group represented by any one of the following formulae (L-1) to (L-12), or a divalent linking group containing 2 or more divalent linking groups each represented by any one of the following formulae (L-1) to (L-12) bonded to each other; and $R^c$ and $R^d$ each independently represent a substituted or unsubstituted alkyl group having 6 to 12 carbon atoms, an oligoethyleneoxy group having a repeating number of an ethyleneoxy unit of 2 or more, or an oligosiloxane group having 2 or more silicon atoms,

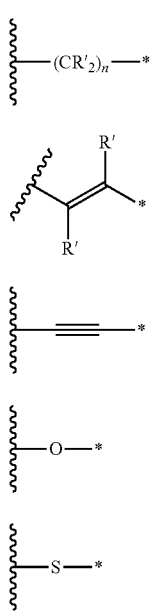

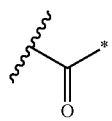

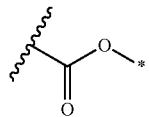

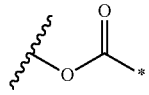

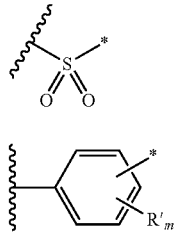

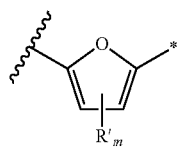

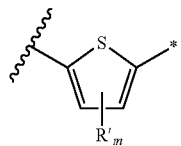

wherein in the formulae (L-1) to (L-12), the wavy line represents a position bonded to the naphthobisbenzofuran skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-2), (L-10), (L-11) and (L-12), R' each independently represent a hydrogen atom or a substituent.

4. The organic thin film transistor according to claim 3, wherein in the formula (2-1) or (2-2), $R^a$, $R^b$, $R^c$ and $R^d$ represent an alkyl group having 6 to 12 carbon atoms.

5. The organic thin film transistor according to claim 3, wherein in the formula (2-1) or (2-2), $R^a$, $R^b$, $R^c$ and $R^d$ represent a linear alkyl group having from 6 to 12 carbon atoms.

6. The organic thin film transistor according to claim 3, wherein in formula (2-1) or (2-2), $L^a$, $L^b$, $L^c$ and $L^d$ represent a single bond.

7. An organic semiconductor material for a non-light emitting organic semiconductor device, containing the compound represented by the following formula (1):

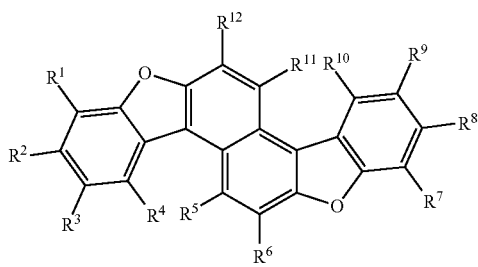

wherein $R^1$ to $R^{12}$ each independently represent a hydrogen atom or a substituent, provided that at least one of $R^1$ to $R^{12}$ represents a substituent represented by the following formula (W), or all of $R^1$ to $R^{12}$ represent a hydrogen atom:

*-L-R           Formula (W)

wherein * represents a position bonded to the naphthobisbenzofuran skeleton; L represents a single bond, a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group having 6 to 12 carbon atoms, an oligoethyleneoxy group having a repeating number of an ethyleneoxy unit of 2 or more, or an oligosiloxane group having 2 or more silicon atoms:

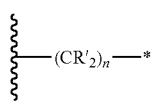 (L-1)

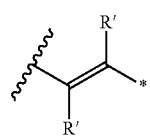 (L-2)

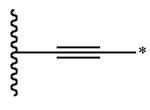 (L-3)

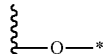 (L-4)

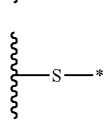 (L-5)

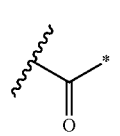 (L-6)

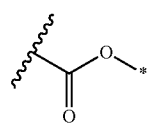 (L-7)

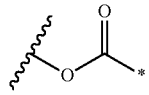 (L-8)

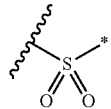 (L-9)

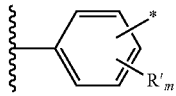 (L-10)

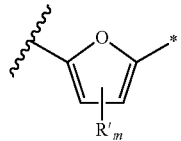 (L-11)

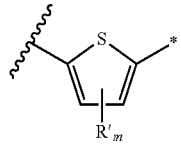 (L-12)

wherein in the formulae (L-1) to (L-12), the wavy line represents a position bonded to the naphthobisbenzofuran skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-2), (L-10), (L-11) and (L-12), R' each independently represent a hydrogen atom or a substituent.

8. A material for an organic thin film transistor, containing the compound represented by the following formula (1):

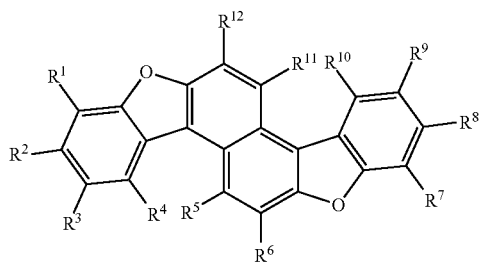

wherein $R^1$ to $R^{12}$ each independently represent a hydrogen atom or a substituent, provided that at least one of $R^1$ to $R^{12}$ represents a substituent represented by the following formula (W), or all of $R^1$ to $R^{12}$ represent a hydrogen atom:

*-L-R           Formula (W)

wherein * represents a position bonded to the naphthobisbenzofuran skeleton; L represents a single bond, a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group having 6 to 12 carbon atoms, an oligoethyleneoxy group having a repeating number of an ethyleneoxy unit of 2 or more, or an oligosiloxane group having 2 or more silicon atoms:

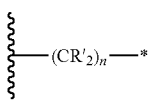
(L-1)

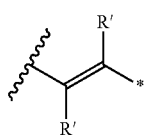
(L-2)

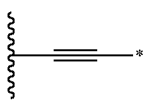
(L-3)

(L-4)

(L-5)

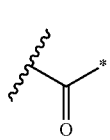
(L-6)

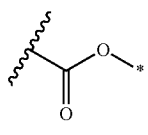
(L-7)

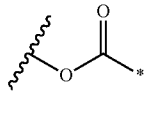
(L-8)

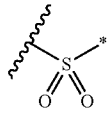
(L-9)

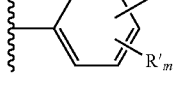
(L-10)

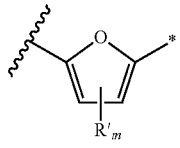
(L-11)

-continued

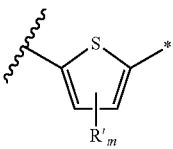
(L-12)

wherein in the formulae (L-1) to (L-12), the wavy line represents a position bonded to the naphthobisbenzofuran skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-2), (L-10), (L-11) and (L-12), R' each independently represent a hydrogen atom or a substituent.

9. A coating solution for a non-light emitting organic semiconductor device, containing the compound represented by the following formula (1):

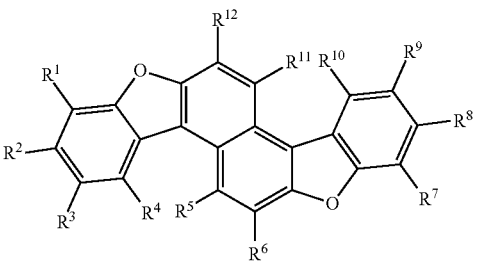

wherein $R^1$ to $R^{12}$ each independently represent a hydrogen atom or a substituent, provided that at least one of $R^1$ to $R^{12}$ represents a substituent represented by the following formula (W), or all of $R^1$ to $R^{12}$ represent a hydrogen atom:

\*-L-R     Formula (W)

wherein * represents a position bonded to the naphthobisbenzofuran skeleton; L represents a single bond, a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group having 6 to 12 carbon atoms, an oligoethyleneoxy group having a repeating number of an ethyleneoxy unit of 2 or more, or an oligosiloxane group having 2 or more silicon atoms:

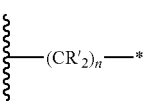
(L-1)

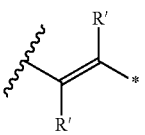
(L-2)

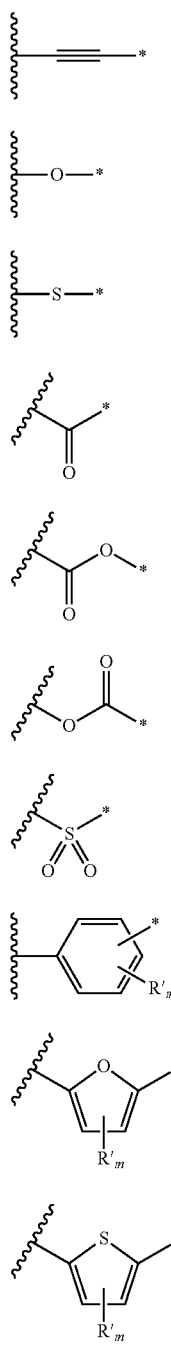

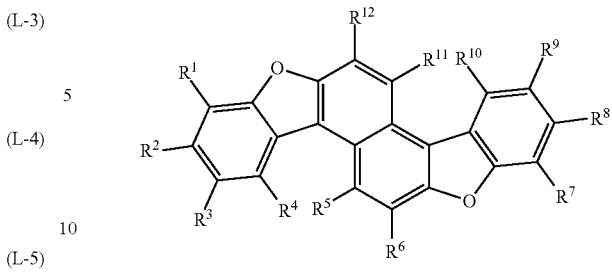

wherein $R^1$ to $R^{12}$ each independently represent a hydrogen atom or a substituent, provided that at least one of $R^1$ to $R^{12}$ represents a substituent represented by the following formula (W), or all of $R^1$ to $R^{12}$ represent a hydrogen atom:

*-L-R  Formula (W)

wherein * represents a position bonded to the naphthobisbenzofuran skeleton; L represents a single bond, a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group having 6 to 12 carbon atoms, an oligoethyleneoxy group having a repeating number of an ethyleneoxy unit of 2 or more, or an oligosiloxane group having 2 or more silicon atoms:

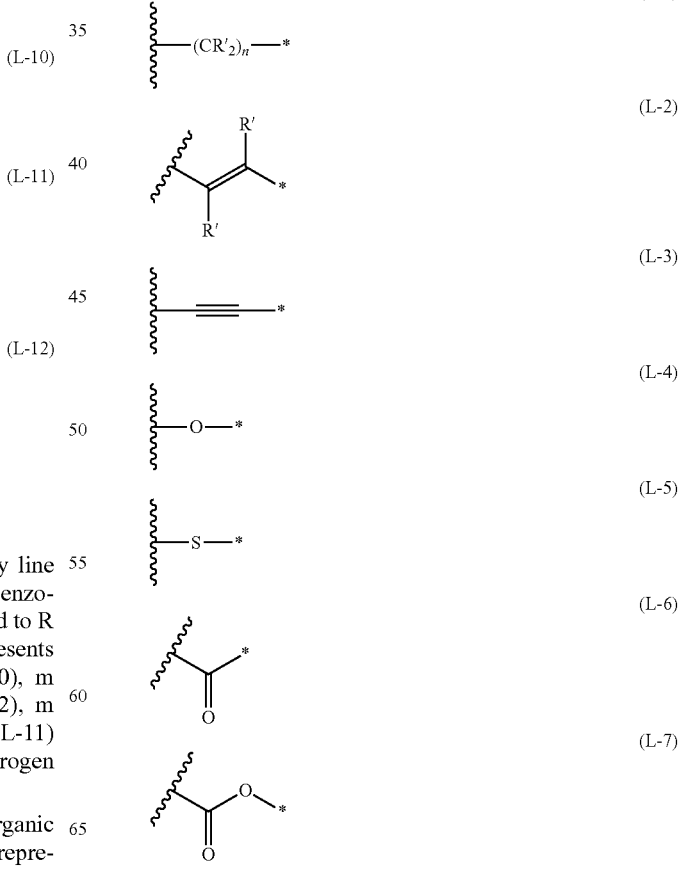

wherein in the formulae (L-1) to (L-12), the wavy line represents a position bonded to the naphthobisbenzofuran skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-2), (L-10), (L-11) and (L-12), R' each independently represent a hydrogen atom or a substituent.

10. A coating solution for a non-light emitting organic semiconductor device, containing the compound represented by the following formula (1):

-continued

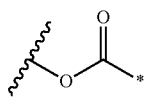 (L-8)

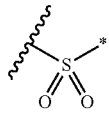 (L-9)

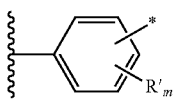 (L-10)

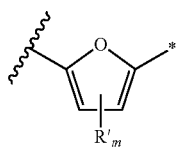 (L-11)

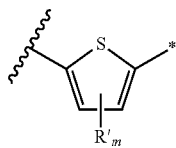 (L-12)

wherein in the formulae (L-1) to (L-12), the wavy line represents a position bonded to the naphthobisbenzofuran skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-2), (L-10), (L-11) and (L-12), R' each independently represent a hydrogen atom or a substituent, and a polymer binder.

11. An organic semiconductor thin film for a non-light emitting organic semiconductor device, containing the compound represented by the following formula (1):

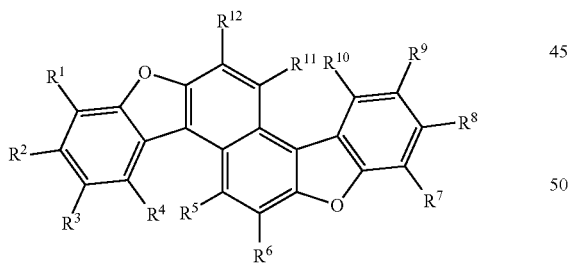

wherein $R^1$ to $R^{12}$ each independently represent a hydrogen atom or a substituent, provided that at least one of $R^1$ to $R^{12}$ represents a substituent represented by the following formula (W), or all of $R^1$ to $R^{12}$ represent a hydrogen atom:

*-L-R  Formula (W)

wherein * represents a position bonded to the naphtho-bisbenzofuran skeleton; L represents a single bond, a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group having 6 to 12 carbon atoms, an oligoethyleneoxy group having a repeating number of an ethyleneoxy unit of 2 or more, or an oligosiloxane group having 2 or more silicon atoms:

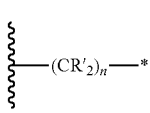 (L-1)

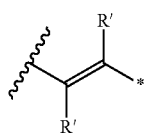 (L-2)

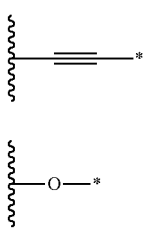 (L-3)

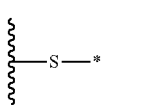 (L-4)

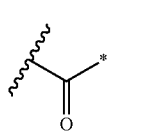 (L-5)

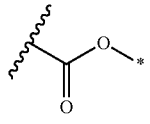 (L-6)

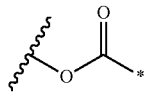 (L-7)

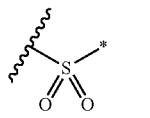 (L-8)

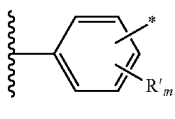 (L-9)

(L-10)

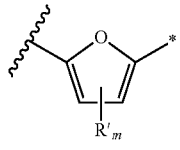 (L-11)

-continued (L-12)

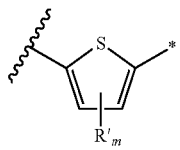

wherein in the formulae (L-1) to (L-12), the wavy line represents a position bonded to the naphthobisbenzofuran skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-2), (L-10), (L-11) and (L-12), R' each independently represent a hydrogen atom or a substituent.

12. An organic semiconductor thin film for a non-light emitting organic semiconductor device, containing the compound represented by the following formula (1):

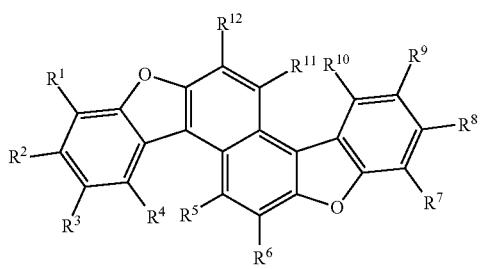

wherein $R^1$ to $R^{12}$ each independently represent a hydrogen atom or a substituent, provided that at least one of $R^1$ to $R^{12}$ represents a substituent represented by the following formula (W), or all of $R^1$ to $R^{12}$ represent a hydrogen atom:

*-L-R   Formula (W)

wherein * represents a position bonded to the naphthobisbenzofuran skeleton; L represents a single bond, a divalent linking group represented by any one of the following formulae (L-1) to (L-12), or a divalent linking group containing 2 or more divalent linking groups each represented by any one of the following formulae (L-1) to (L-12) bonded to each other; and R represents a substituted or unsubstituted alkyl group having 6 to 12 carbon atoms, an oligoethyleneoxy group having a repeating number of an ethyleneoxy unit of 2 or more, or an oligosiloxane group having 2 or more silicon atoms:

(L-1)

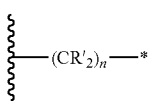

(L-2)

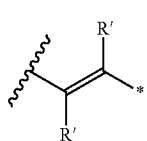

(L-3)

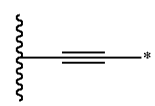

(L-4)

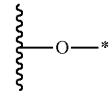

(L-5)

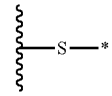

(L-6)

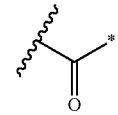

(L-7)

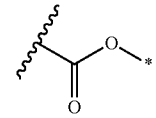

(L-8)

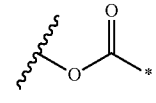

(L-9)

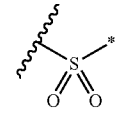

(L-10)

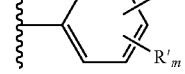

(L-11)

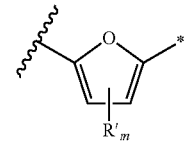

(L-12)

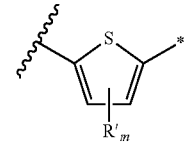

wherein in the formulae (L-1) to (L-12), the wavy line represents a position bonded to the naphthobisbenzofuran skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-2), (L-10), (L-11) and (L-12), R' each independently represent a hydrogen atom or a substituent, and a polymer binder.

13. The organic semiconductor thin film for a non-light emitting organic semiconductor device according to claim 11 which is produced by a solution coating method.

14. The organic thin film transistor according to claim 1, wherein the compound represented by the formula (1) is a compound represented by the following formula (2-1) or (2-2):

Formula (2-1)

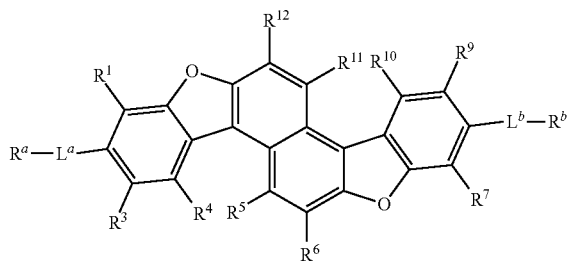

wherein $R^1$, $R^3$ to $R^7$, and $R^9$ to $R^{12}$ each independently represent a hydrogen atom or a substituent; $L^a$ and $L^b$ each independently represent a single bond, a divalent linking group represented by any one of the following formulae (L-1) to (L-12), or a divalent linking group containing 2 or more divalent linking groups each represented by any one of the following formulae (L-1) to (L-12) bonded to each other; and $R^a$ and $R^b$ each independently represent a substituted or unsubstituted alkyl group having 2 or more carbon atoms, an oligoethyleneoxy group having a repeating number of an ethyleneoxy unit of 2 or more, or an oligosiloxane group having 2 or more silicon atoms, Formula (2-2)

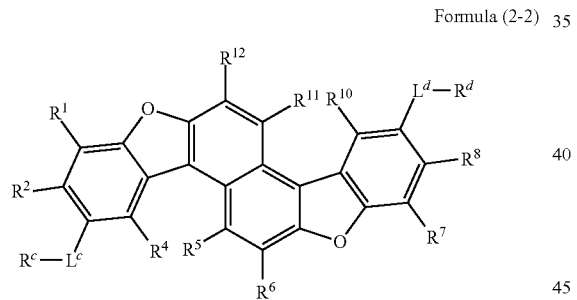

wherein $R^1$, $R^2$, $R^4$ to $R^8$, and $R^{10}$ to $R^{12}$ each independently represent a hydrogen atom or a substituent; $L^c$ and $L^d$ each independently represent a single bond, a divalent linking group represented by any one of the following formulae (L-1) to (L-12), or a divalent linking group containing 2 or more divalent linking groups each represented by any one of the following formulae (L-1) to (L-12) bonded to each other; and $R^c$ and $R^d$ each independently represent a substituted or unsubstituted alkyl group having 2 or more carbon atoms, an oligoethyleneoxy group having a repeating number of an ethyleneoxy unit of 2 or more, or an oligosiloxane group having 2 or more silicon atoms, (L-1)

(L-2)

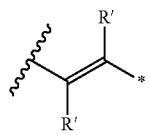

(L-3)

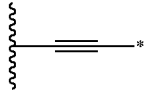

(L-4)

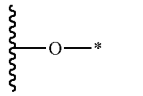

(L-5)

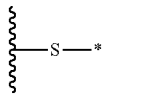

(L-6)

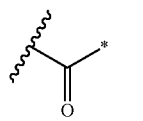

(L-7)

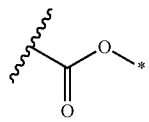

(L-8)

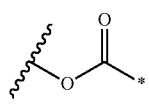

(L-9)

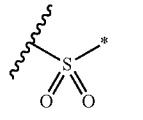

(L-10)

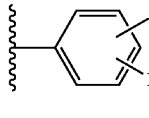

(L-11)

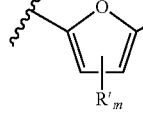

(L-12)

wherein in the formulae (L-1) to (L-12), the wavy line represents a position bonded to the naphthobisbenzofuran skeleton, and * represents a position bonded to R in the formula (W); in the formula (L-1), n represents an integer of 1 or more; in the formula (L-10), m represents 4; in the formulae (L-11) and (L-12), m represents 2; and in the formulae (L-2), (L-10), (L-11) and (L-12), R' each independently represent a hydrogen atom or a substituent, wherein in the formula (2-1) or (2-2), $R^a$, $R^b$, $R^c$ and $R^d$ represent a linear alkyl group having from 6 to 12 carbon atoms, and wherein the number of the substituent other than the substituent represented by the formula (W) in $R^1$ to $R^{12}$ is 0.

* * * * *